United States Patent [19]
Sumner, Jr. et al.

[11] Patent Number: 6,159,347
[45] Date of Patent: Dec. 12, 2000

[54] METHODS FOR SEPARATING A TOCOL FROM A TOCOL-CONTAINING MIXTURE

[75] Inventors: Charles E. Sumner, Jr., Kingsport; John D. Moncier, Church Hill, both of Tenn.; Jeffrey S. Kanel, Hurricane, W. Va.; Mary K. Foster, Jonesborough, Tenn.

[73] Assignee: Eastman Chemical Company, Kingsport, Tenn.

[21] Appl. No.: 09/237,406

[22] Filed: Jan. 26, 1999

Related U.S. Application Data

[60] Provisional application No. 60/072,962, Jan. 29, 1998, and provisional application No. 60/072,963, Jan. 29, 1998.

[51] Int. Cl.$^7$ .............................. B01D 11/00; B01D 3/00; C07D 311/04
[52] U.S. Cl. ................................ 203/43; 203/74; 549/413
[58] Field of Search .............................. 549/413; 203/43, 203/74

[56] References Cited

U.S. PATENT DOCUMENTS

| | | |
|---|---|---|
| 2,866,797 | 12/1958 | Berry et al. . |
| 3,153,055 | 10/1964 | Brown et al. . |
| 3,335,154 | 8/1967 | Smith . |
| 4,454,329 | 6/1984 | Takagi et al. . |
| 4,480,108 | 10/1984 | Foster . |
| 4,550,183 | 10/1985 | Willging . |
| 5,487,817 | 1/1996 | Fizet . |
| 5,512,691 | 4/1996 | Barnicki et al. . |
| 5,660,691 | 8/1997 | Barnicki et al. . |
| 5,670,669 | 9/1997 | Hunt . |
| 5,908,940 | 6/1999 | Lane et al. . |

FOREIGN PATENT DOCUMENTS

| | | |
|---|---|---|
| 01971009 | 2/1986 | European Pat. Off. . |
| 333472 | 9/1989 | European Pat. Off. . |
| 610742 | 8/1994 | European Pat. Off. . |
| 3615029 A1 | 11/1986 | Germany . |
| 60048981 | 3/1985 | Japan . |
| 60149582 | 8/1985 | Japan . |
| 60185776 | 9/1985 | Japan . |
| 61093178 | 5/1986 | Japan . |
| 3127730 | 5/1991 | Japan . |
| WO 97/21697 | 6/1997 | WIPO . |

*Primary Examiner*—Cecilia Tsang
*Assistant Examiner*—Joseph Murray
*Attorney, Agent, or Firm*—Cheryl J. Tubach; Harry J. Gwinnell

[57] ABSTRACT

The invention relates to method for separating tocol from a tocol-containing admixture by heating the tocol-containing admixture composed a tocol, a fatty acid, and an esterifying compound to esterify the fatty acid to produce a second tocol admixture composed of the tocol, the esterified fatty acid, and the unesterified fatty acid; distilling the tocol-containing admixture with the esterified fatty acid to remove the unesterified fatty acid from the tocol admixture to produce a tocol admixture composed of the tocol with substantially removed unesterified fatty acid; distilling the tocol admixture for a sufficient time and temperature to substantially remove the tocol from the tocol admixture to produce a tocol admixture composed of the removed tocol and a non-tocol component; and extracting the tocol from the tocol admixture with an extraction solvent composed of a polar, organic solvent that is miscible with water to produce a two phase system composed of a first phase containing the majority of the extraction solvent and the second phase, wherein the selectivity of the extraction solvent for tocol with respect to the non-tocol component is greater than unity, and removing the first phase from the second phase, with the proviso that the extraction solvent is not a neat alcohol.

60 Claims, 1 Drawing Sheet

METHODS FOR SEPARATING A TOCOL FROM A TOCOL-CONTAINING MIXTURE

CROSS REFERENCE TO RELATED APPLICATIONS

This application claims priority upon United States provisional application serial nos. 60/072,962 and 60/072,963, both filed on Jan. 29, 1998, and the contents of which are herein incorporated by this reference in their entirety.

FIELD OF THE INVENTION

The present invention relates to methods for separating a tocol from a tocol-containing mixture.

BACKGROUND

Alpha, beta, gamma, and delta tocopherol and alpha, beta, gamma, and delta tocotrienol (hereafter such tocopherols and tocotrienols are referred to collectively as tocols) can be found in various ratios and concentrations in crude vegetable oils such as soybean, sunflower, canola, rapeseed, cottonseed, palm oil, and rice bran oil. Tocols are valuable constituents of vegetable oil and have a number of practical applications. For example, tocols help prevent the oxidation and spoilage of food. Tocols are also valuable dietary supplements because they can reduce the risk of certain types of cancer.

During the refining of vegetable oils, a large fraction of tocols are lost to various by-product and waste streams. These by-product and waste streams include, but are not limited to, deodorizer distillates, steam refining distillates, and acidulated soapstocks. The vegetable oil refining by-products typically contain from less than 1% to greater than 20% tocols by weight. Thus, the oil refining by-products are a valuable source of tocols.

The by-product streams that contain the tocols also contain from 20 to 99% by weight free fatty acids, less than 1% to 20% by weight sterols, less than 1% to 20% by weight sterol esters of fatty acid, less than 1% to 40% by weight mono, di, and triglycerides, less than 1% to 30% by weight hydrocarbons, and other compounds present in significant amounts. Thus, in order to obtain a useful tocol concentrate stream, it is necessary to remove these substances.

Numerous methods have been proposed for the recovery of tocols from vegetable oil refining by-products. Tocols can be removed from tocol-containing mixtures by subjecting the mixture to a series of distillations. U.S. Pat. Nos. 5,512,691; 5,660,691; and 5,487,817 disclose that a tocol concentrate can be obtained from a deodorizer distillate by esterification of the sterols with the free fatty acids already present in the mixture, and subjecting the esterified product to a series of distillation steps to provide a tocol concentrate stream. EP 610742 A and JP 60185776 A also disclose the separation of tocopherols from fat residues using distillation techniques. None of these references, however, disclose an extraction step for separating a tocol from a tocol-containing mixture.

JP60048981A and JP60149582A discloses that tocopherols can be concentrated by extraction of a tocopherol containing substance with supercritical carbon dioxide, which is a non-polar, organic solvent that is immiscible with water under supercritical conditions. Moreover, these methods require the use of expensive, high-pressure equipment capable of withstanding pressures of at least 73 bar.

DE 3615029 discloses the purification of tocopherols by contacting a tocopherol containing substance with neat methanol to form two layers, separating the methanol layer, cooling the methanol layer to produce a methanol phase and a raffinate layer, and recovering the tocopherols from the methanol layer. A disadvantage of this method is that a considerable amount of tocopherols are lost to the raffinate, thereby reducing the overall recoverable yield. U.S. Pat. No. 4,550,183 discloses extracting a tocopherol containing material with caustic methanol to produce a two phase system. The methanol layer is removed and neutralized with acid. A disadvantage of this method is that an additional step is required to neutralize the basic methanol layer. JP 03127730 A discloses extracting an unsaturated oil or fat with a neat extraction solvent composed of neat butanol, ethylene glycol, methyl ethyl ketone, acetone, benzene, or cyclohexane followed by a series of distillation steps.

Another approach for increasing the concentration of tocols is to add an esterifying agent such as an alcohol to convert the free fatty acids present in the tocol-containing mixture to the corresponding ester followed by distillation to remove the tocol. For example, U.S. Pat. No. 2,432,181 discloses that tocopherols can be recovered from vegetable oils and fats by reacting the fatty acid glycerides with an aliphatic monohydric alcohol in the presence of an alkaline alcoholysis catalyst, followed by a flash distillation. U.S. Pat. No. 3,153,055 discloses a process for the isolation of sterols and tocopherols from deodorizer distillate by esterification of free fatty acids and glycerides using lower monohydric alcohol esters under strongly acidic conditions. U.S. Pat. No. 3,335,154 discloses that deodorizer distillate is saponified and acidulated to convert glycerides and sterol esters to free fatty acids and free alcohols (glycerol, sterols respectively). The free fatty acids are esterified with a monohydric lower alcohol and mineral acid catalyst. The sterols are precipitated/crystallized by the addition of water to the mixture, and the tocopherols are concentrated by removal of the fatty acid esters by molecular distillation. U.S. Pat. No. 4,454,329 describes that a tocopherol concentrate can be obtained from deodorizer distillates by esterification of the free fatty acids with a dihydric or polyhydric alcohol, in the presence or absence of an acid catalyst.

The addition of alcohols has a number of drawbacks. The addition of extraneous monohydric alcohols results in the production of fatty acid esters, which are not normally present in the vegetable oil by-product feed material. The excess monohydric alcohol must be removed in an additional processing step. Additionally, to produce a highly concentrated tocopherol product, the sterols must either be removed by crystallization or by other means. Finally, saponification of the fatty acids requires large amounts of caustic acid for acidulation, which creates excessive salt wastes.

In light of the above, one object of this invention is to provide an efficient method for separating tocols from a tocol-containing mixture.

Another object of the present invention is to provide a method for separating tocotrienols from a tocol-containing mixture. Tocotrienols have been shown to treat or prevent a number of human diseases. Preliminary medical research has shown that tocotrienols, particularly gamma-tocotrienol, can reduce the proliferation of breast cancer especially when used in conjunction with other anti-cancer drugs (Nesaretnam K, Guthrie N, Chambers A F, and Carrol K K *Lipids* 1995 30 1139; and Guthrie N, Gapor A, Chambers A F, and Carroll K K *J. Nutr.* 1997 127 544S). Tocotrienols are also of special interest for their hypocholesterolemic effects, as they decrease the blood level of the low density lipoprotein fraction of cholesterol and the total serum cholesterol, while increasing the ratio of the high density lipoprotein fraction of cholesterol to the low density lipoprotein fraction. Such effects have been shown to be clinically significant in lowering the risk of heart disease. (T. Gordon, et al., "High Density Lipoproteins as a Protective Factor Against Coronary Heart Disease", *The American Journal of Medicine*, 62, pp. 707–714 (1977)).

Thus, it would be desirable to have a method for isolating increased quantities of tocotrienols.

Another object of the present invention is to provide a method for separating tocopherols from a tocol-containing mixture. In particular, alpha-tocopherol can reduce the risk of stomach and prostrate cancer. Thus, there is presently a high demand for increased quantities of tocopherols.

The prior art methods for increasing the tocol concentration are inefficient with respect to the number of steps required to separate the tocols as well as the overall yield of the recovered tocols. Additionally, there are no explicit methods in the prior art for the production of increased quantities of tocotrienols. The present invention discloses efficient methods for separating tocols and/or tocotrienols from a tocol-containing mixture.

SUMMARY OF THE INVENTION

In accordance with the purpose(s) of this invention, as embodied and broadly described herein, this invention, in one aspect, relates to a method for separating a tocotrienol from a first tocol admixture comprising at least one tocotrienol and at least one tocopherol, a first fatty acid, and an esterifying compound, comprising (a) heating the first tocol admixture comprising the tocotrienol, the tocopherol, the first fatty acid, and the esterifying compound for a sufficient time and temperature to substantially esterify the first fatty acid with the esterifying compound to produce a second tocol admixture comprising the tocotrienol, the tocopherol, esterified first fatty acid, and unesterified first fatty acid;

(b) distilling the second tocol admixture for a sufficient time and temperature to substantially remove the unesterified first fatty acid from the second tocol admixture to produce a third tocol admixture comprising the tocotrienol, the esterified first fatty acid, and the tocopherol, with substantially removed unesterified first fatty acid;

(c) distilling the third tocol admixture for a sufficient time and temperature to substantially remove the tocotrienol and the tocopherol from the third tocol admixture to produce a fourth tocol admixture comprising the removed tocotrienol, the tocopherol, and a non-tocol component; and (d) extracting the tocotrienol from the fourth tocol admixture with an extraction solvent comprising a polar, organic solvent that is miscible with water to produce a two phase system comprising a first phase containing a majority of the extraction solvent and a second phase, wherein the selectivity of the extraction solvent for the tocotrienol with respect to the tocopherol is greater than unity, and removing the first phase from the second phase, with the proviso that the extraction solvent is not a neat alcohol, wherein step (b) can be conducted before step (c), or step (c) can be conducted before step (b), wherein steps (b) and (c) are conducted after step (a) and prior to step (d).

The invention further relates to a method for separating tocotrienol from a tocol admixture comprising tocotrienol and at least one tocopherol, comprising extracting tocotrienol from the tocol admixture with an extraction solvent comprising an aqueous composition comprising water and a polar, organic solvent that is miscible with water to produce a two phase system comprising a first phase containing a majority of the extraction solvent and a second phase, wherein the selectivity of the extraction solvent for the tocotrienol with respect to the tocopherol is greater than unity, and removing the first phase from the second phase, with the proviso that the extraction solvent does not comprise an alcohol.

The invention further relates to compositions produced by the above methods of the present invention.

The invention further relates to a composition comprising gamma-tocotrienol and alpha-tocopherol, wherein the ratio of gamma-tocotrienol to alpha-tocopherol is from 1:1 to 10:1.

The invention further relates to a method for separating a tocol from a first tocol admixture comprising at least one tocol, a first fatty acid, and an esterifying compound, comprising (a) heating the first tocol admixture comprising the tocol, the first fatty acid, and the esterifying compound for a sufficient time and temperature to substantially esterify the first fatty acid with the esterifying compound to produce a second tocol admixture comprising the tocol, esterified first fatty acid, and unesterified first fatty acid;

(b) distilling the second tocol admixture for a sufficient time and temperature to substantially remove the unesterified first fatty acid from the second tocol admixture to produce a third tocol admixture comprising the tocol and esterified fatty acid with substantially removed unesterified first fatty acid;

(c) distilling the third tocol admixture for a sufficient time and temperature to substantially remove the tocol from the third tocol admixture to produce a fourth tocol admixture comprising the removed tocol and a non-tocol component; and (d) extracting the tocol from the fourth tocol admixture with an extraction solvent comprising a polar, organic solvent that is miscible with water to produce a two phase system comprising a first phase containing a majority of the extraction solvent and a second phase, wherein the selectivity of the extraction solvent for the tocol with respect to the non-tocol component of the fourth tocol admixture is greater than unity, and removing the first phase from the second phase, with the proviso that the extraction solvent is not a neat alcohol, wherein step (b) can be conducted before step (c), or step (c) can be conducted before step (b), wherein steps (b) and (c) are conducted after step (a) and prior to step (d).

The invention further relates to a method for separating a tocol from a tocol admixture comprising at least one tocol and a non-tocol component, comprising extracting the tocol from the tocol admixture with an extraction solvent comprising an aqueous composition comprising water and a polar, organic solvent that is miscible with water to produce a two phase system comprising a first phase containing a majority of the extraction solvent and a second phase, wherein the selectivity of the extraction solvent for the tocol with respect to the non-tocol component of the tocol admixture is greater than unity, and removing the first phase from the second phase, with the proviso that the extraction solvent does not comprise an alcohol.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Figure 1:
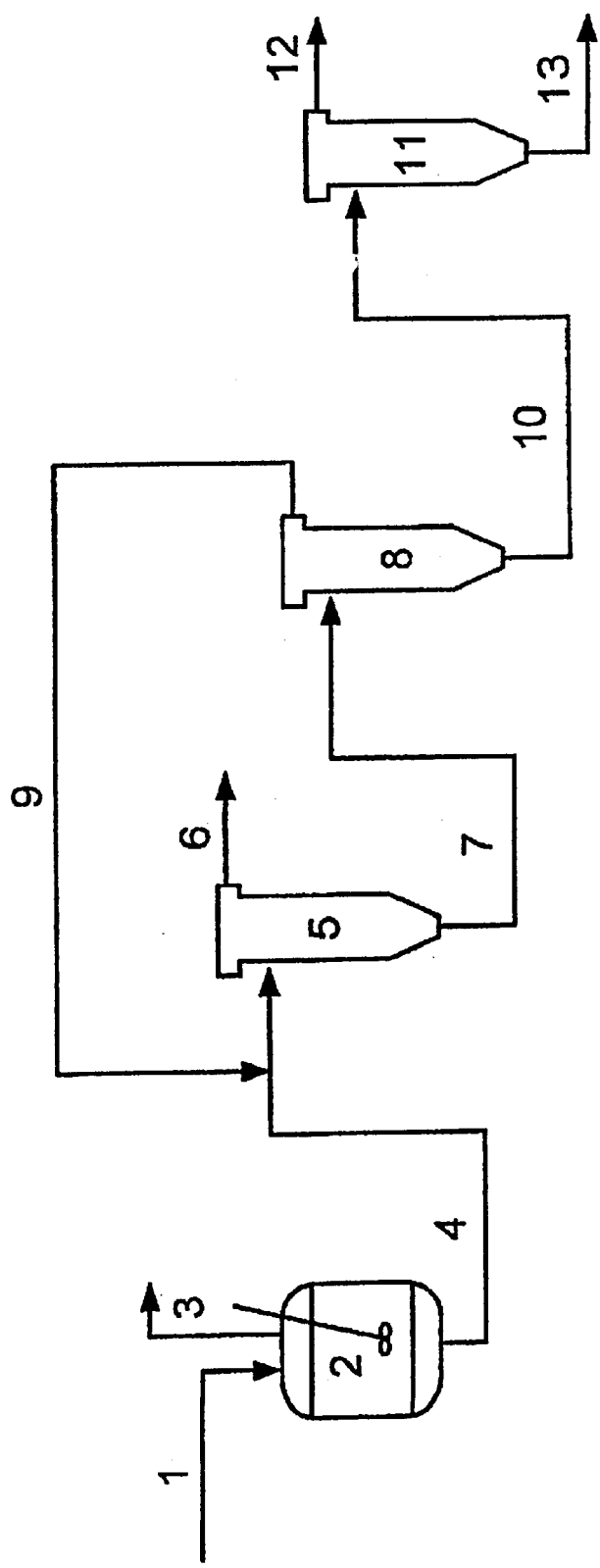
FIG. 1 is one embodiment of the present invention, which shows the typical distillation steps (a)–(c) of the present invention.

also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

The term "tocol" is defined as any tocopherol or tocotrienol known in the art. The term "tocols" is defined as two or more tocopherols or tocotrienols, or at least one tocopherol and at least one tocotrienol. Examples of tocopherols include all tocopherols such as alpha-tocopherol, beta-tocopherol, gamma-tocopherol, and delta-tocopherol. Examples of tocotrienols include all tocotrienols such as alpha-tocotrienol, beta-tocotrienol, gamma-tocotrienol, and delta-tocotrienol. The structures of all of these tocopherols and tocotrienols are well known to those of skill in the art.

"Gamma-tocotrienol" has the structure (I) shown below:

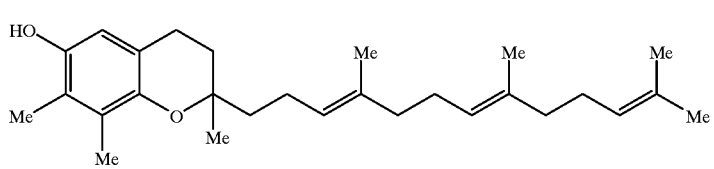

"Alpha-tocopherol" has the structure (II) shown below:

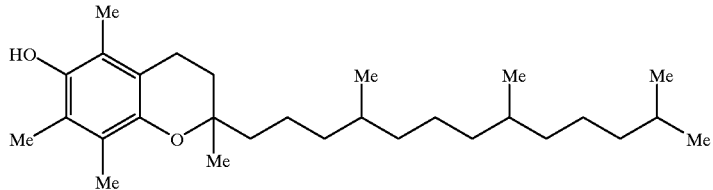

DETAILED DESCRIPTION OF THE INVENTION

The present invention may be understood more readily by reference to the following detailed description of preferred embodiments of the invention and the Examples included therein.

Before the present compositions of matter and methods are disclosed and described, it is to be understood that this invention is not limited to specific synthetic methods or to particular formulations, as such may, of course, vary. It is The term "separating" is defined as increasing the amount of one substance relative to one or more other substances. For example, if a first mixture has 50% A and 40% B, when B is "separated" from the first mixture, a second mixture is produced, wherein the second mixture is composed of 20% A and 40% B. In this example, the amount of B has increased relative to the amount of A. The term "separating" can also include the isolation of only one compound from a mixture of two or more compounds.

The phrase "polar, organic solvent that is miscible with water" is defined herein as any polar, organic compound that is at least 5%, more preferably 10%, more preferably 25%, more preferably 50%, more preferably 75%, more preferably 100% by weight soluble in water at 25° C.

In accordance with the purpose(s) of this invention, as embodied and broadly described herein, this invention, in one aspect, relates to a method for separating a tocotrienol from a first tocol admixture comprising at least one tocotrienol and at least one tocopherol, a first fatty acid, and an esterifying compound, comprising (a) heating the first tocol admixture comprising the tocotrienol, the tocopherol, the first fatty acid, and the esterifying compound for a sufficient time and temperature to substantially esterify the first fatty acid with the esterifying compound to produce a second tocol admixture comprising the tocotrienol, the tocopherol, esterified first fatty acid, and unesterified first fatty acid;

(b) distilling the second tocol admixture for a sufficient time and temperature to substantially remove the unesterified first fatty acid from the second tocol admixture to produce a third tocol admixture comprising the tocotrienol, the esterified first fatty acid, and the tocopherol, with substantially removed unesterified first fatty acid;

(c) distilling the third tocol admixture for a sufficient time and temperature to substantially remove the tocotrienol and the tocopherol from the third tocol admixture to produce a fourth tocol admixture comprising the removed tocotrienol, the tocopherol, and a non-tocol component; and (d) extracting the tocotrienol from the fourth tocol admixture with an extraction solvent comprising a polar, organic solvent that is miscible with water to produce a two phase system comprising a first phase containing a majority of the extraction solvent and a second phase, wherein the selectivity of the extraction solvent for the tocotrienol with respect to the tocopherol is greater than unity, and removing the first phase from the second phase, with the proviso that the extraction solvent is not a neat alcohol, wherein step (b) can be conducted before step (c), or step (c) can be conducted before step (b), wherein steps (b) and (c) are conducted after step (a) and prior to step (d).

The invention further relates to a method for separating tocotrienol from a tocol admixture comprising tocotrienol and at least one tocopherol, comprising extracting tocotrienol from the tocol admixture with an extraction solvent comprising an aqueous composition comprising water and a polar, organic solvent that is miscible with water to produce a two phase system comprising a first phase containing a majority of the extraction solvent and a second phase, wherein the selectivity of the extraction solvent for the tocotrienol with respect to the tocopherol is greater than unity, and removing the first phase from the second phase, with the proviso that the extraction solvent does not comprise an alcohol.

The invention further relates to compositions produced by the above methods of the present invention.

The invention further relates to a composition comprising gamma-tocotrienol and alpha-tocopherol, wherein the ratio of gamma-tocotrienol to alpha-tocopherol is from 1:1 to 10:1.

The invention further relates to a method for separating a tocol from a first tocol admixture comprising at least one tocol, a first fatty acid, and an esterifying compound, comprising (a) heating the first tocol admixture comprising the tocol, the first fatty acid, and the esterifying compound for a sufficient time and temperature to substantially esterify the first fatty acid with the esterifying compound to produce a second tocol admixture comprising the tocol, esterified first fatty acid, and unesterified first fatty acid;

(b) distilling the second tocol admixture for a sufficient time and temperature to substantially remove the unesterified first fatty acid from the second tocol admixture to produce a third tocol admixture comprising the tocol and esterified fatty acid with substantially removed unesterified first fatty acid;

(c) distilling the third tocol admixture for a sufficient time and temperature to substantially remove the tocol from the third tocol admixture to produce a fourth tocol admixture comprising the removed tocol and a non-tocol component; and (d) extracting the tocol from the fourth tocol admixture with an extraction solvent comprising a polar, organic solvent that is miscible with water to produce a two phase system comprising a first phase containing a majority of the extraction solvent and a second phase, wherein the selectivity of the extraction solvent for the tocol with respect to the non-tocol component of the fourth tocol admixture is greater than unity, and removing the first phase from the second phase, with the proviso that the extraction solvent is not a neat alcohol, wherein step (b) can be conducted before step (c), or step (c) can be conducted before step (b), wherein steps (b) and (c) are conducted after step (a) and prior to step (d).

The invention further relates to a method for separating a tocol from a tocol admixture comprising at least one tocol and a non-tocol component, comprising extracting the tocol from the tocol admixture with an extraction solvent comprising an aqueous composition comprising water and a polar, organic solvent that is miscible with water to produce a two phase system comprising a first phase containing a majority of the extraction solvent and a second phase, wherein the selectivity of the extraction solvent for the tocol with respect to the non-tocol component of the tocol admixture is greater than unity, and removing the first phase from the second phase, with the proviso that the extraction solvent does not comprise an alcohol.

Composition of Tocol-Containing Mixture

The first tocol admixture can be any composition that contains a tocol. Typically, the first tocol admixture comprises one or more tocotrienols and one or more tocopherols. In one embodiment, the first tocol admixture comprises nut oil or animal oil. In another embodiment, the first tocol admixture is the waste stream or by-product of vegetable oil refining. Examples of waste and by-product streams include, but are not limited to, deodorizer distillates, steam refining distillates, and acidulated soapstocks. In one embodiment, the first tocol admixture comprises vegetable oil deodorizer distillate. Examples of vegetable oil deodorizer distillates that contain tocols include, but are not limited to palm oil, rice bran oil, or soybean oil deodorizer distillates. In a preferred embodiment, the first tocol admixture comprises rice bran oil deodorizer distillate. The vegetable oil refining by-products typically contain from less than 1% to greater than 20% tocols by weight. The deodorizer distillate typically contains from about 0.1 to 5% by weight tocotrienols. The deodorizer distillate can be obtained using techniques known in the art.

The first tocol admixture also includes waxes, which have similar boiling points as the tocols. The composition of the wax can vary depending upon the oil. Typically, the wax is composed of dehydrated sterols, linear hydrocarbons, such as nonacosane ($C_{29}H_{60}$), and squalene. Since the waxes have boiling points similar to tocols, they cannot be separated by distillation. Although separation of the tocols from the waxes is possible by chromatography, it is an expensive process. Thus, the present invention utilizes an extraction step to separate the tocols and/or more specifically the tocotrienols from the first tocol admixture, which is an inexpensive and efficient method when compared to prior art techniques.

Esterification and Distillation Steps

In one embodiment, the first tocol admixture is initially heated and then subjected to a series of distillations in order to separate the tocols from the first tocol admixture. The procedure disclosed in U.S. Pat. No. 5,660,691 to Barnicki et al., which is incorporated by this reference in its entirety, can be used to convert the first tocol admixture to the fourth tocol admixture. FIG. 1 is a flow diagram that shows this embodiment of the present invention. The first tocol admixture is fed via line (1) to a stirred tank or batch reactor (2), operating at a temperature of from 70 to 300° C., preferably in the range of from 150 to 230° C., and at a pressure of from 20 torr to 760 torr, preferably from 20 to 200 torr. In one embodiment, the residence time in the reactor is from two to ten hours.

An esterification catalyst can optionally be added to the first tocol admixture prior to heating in line (1). In another embodiment, the esterification catalyst can be added in reactor (2). Examples of esterification catalysts useful in the present invention include, but are not limited to, monoalkyl tin compounds, zinc salt of an organic acid, titanium (IV) alkoxides, zinc oxide, phosphoric acid and other mild mineral acids. When an esterification catalyst is used, the residence time in the reactor can be typically from 1 to 24 hours, preferably from 90 minutes to two hours.

Not wishing to be bound by theory, it is believed that during the heating step (a), the fatty acids, which are present in the first tocol admixture, react with an esterifying compound to produce an esterified first fatty acid. The first fatty acid present in the first tocol admixture includes, but is not limited to, oleic acid, linoleic acid, linolic acid, steric acid, palmitic acid, linolenic acid, and other $C_{16}$, $C_{18}$, and $C_{20}$ or greater carboxylic acids. Any compound present in the first tocol admixture that is capable of esterifying the fatty acids is considered an esterifying compound. Examples of esterifying compounds present in the first tocol admixture include, but are not limited to, sterols, triterpenoid alcohols, or mono- and di-fatty acid esters of glycerol. The tocols may also react to a limited extent with the first fatty acid to form tocol esters and water. The relative rates of the esterification reactions is glycerides>sterols>tocols. Thus, the esterification of tocols can be controlled by the proper selection of reaction temperature and time. In one embodiment, 75% to 100%, typically from 85% to 95% of the sterols are converted to the sterol esters after the heating step. One object of the present invention is to remove the sterols from the tocol admixture prior to distillation because it is difficult to separate the tocols and the sterols by distillation. If the sterols are not removed, the final tocol concentration will be reduced due to the presence of the sterols. In another embodiment, 80 to 97%, typically from 85 to 92% of the tocols are recovered from the first tocol admixture after the heating step.

In another embodiment, a second fatty acid comprising a $C_{14}$–$C_{22}$ fatty acid is added to the first tocol admixture prior to the heating step. The second fatty acid typically comprises palmitic acid, oleic acid, linoleic acid, linolenic acid, or a combination thereof. Up to 40% by weight second fatty acid is preferably added to the first tocol admixture based on the total weight of the first tocol admixture.

Alternatively, the reactor (2) is provided with a means for removal of the water produced during the heating step. The removal of the water by line (3) drives the reaction equilibrium toward the formation of the fatty acid ester products.

The second tocol admixture (stream (4)) is then subjected to a series of distillation steps, wherein components having boiling points higher and lower than the tocols are separated from the second tocol admixture. Steps (b) and (c) of the present invention can be switched. In one embodiment, step (b) is conducted before step (c). In one embodiment, the distillation steps are one or more separate distillation operations to remove the unesterified free fatty acids from the heating step (a). In a preferred embodiment, there are two distillation steps. The order of the distillation steps required to remove the low boilers (e.g. unesterified fatty acid) and the high-boilers (e.g. tocols, sterols, and waxes) does not have to be fixed. Typically, the sterol esters and triglycerides do not boil at the temperatures at which the distillation steps are conducted and, thus, remain in the bottoms.

In one embodiment, the second tocol admixture is distilled in order to remove the unesterified fatty acid to produce a third tocol admixture. Distillation step (b) is conducted in unit (5) under high vacuum to substantially remove the unesterified fatty acid. The unesterified fatty acid is typically removed at from 50 to 90%, more preferably from 60 to 80%, from the second tocol admixture. The unesterified fatty acid along with other low-boilers (stream (6)) are removed to produce a third tocol admixture enriched with tocols (stream (7)). The distillation step (b) is conducted at temperatures and pressures such that the third tocol admixture is left in the bottoms product. In one embodiment, the temperature and pressure of distillation step (b) is generally in the range of from 125° C. to 300° C. and at 0.05 to 10 torr. In a preferred embodiment, the temperature and pressure range is from 150° C. to 200° C. and at 0.5 to 4 torr. Preferably, the distillation apparatus (5) is a high-vacuum design that has a short path evaporator, a wiped-film evaporator, a centrifugal molecular still, or a falling film evaporator capable of low pressure operation.

The third tocol admixture (stream (7)), produced from distillation step (b), can optionally be distilled a second time in distillation operation (8) (step (b')) under high vacuum to remove any remaining unesterified fatty acids and other low-boiling compounds. The temperature of distillation step (b') should be higher or the pressure lower than distillation step (b) in order to ensure essentially complete removal of any remaining unesterified fatty acids. The temperature and pressure of distillation step (b') is in the range of from 125° C. to 300° C. and at 0.01 to 5 torr. The preferred temperature and pressure range is from 150° C. to 220° C. and at 0.1 to 2 torr, more preferably from 150° C. to 200° C. and at 0.1 to 2 torr. Under these conditions a small amount of the tocols will distill overhead with the remaining unesterified fatty acids into stream (9), leaving a tocol-rich bottoms product (10). The distillate (9), which contains some tocols and the remaining free fatty acid may be discarded or recycled to reactor (2) or the first distillation operation (5) in order to improve the overall yield of the tocols. Since distillation (5) and distillation (8) are conducted under different temperature and pressure conditions, they act in combination as a multi-equilibrium staged device, which reduces tocol loss and increases fatty acid removal. The distillation apparatus (8) may be any high-vacuum design including, but not limited to, a short path evaporator, wiped-film evaporator, centrifugal molecular still, or falling film evaporator.

The third tocol admixture (streams (7) or (10)) is subjected to distillation step (c) (11). The tocols and other similarly boiling compounds described above are collected as a final tocol-rich distillate product (12). The triglycerides, sterol esters, other high-boiling fatty acid esters, and other high-boiling compounds are removed in the largely tocol-free bottoms (13) of the distillation. When the esterification catalyst is used, it is removed in the residue through stream (13). In one embodiment, the temperature and pressure of distillation step (c) is in the range of from 150° C. to 270° C. and 0.005 to 2 torr. In a preferred embodiment, the temperature and pressure range is from 190° C. to 250° C. and 0.01 torr to 0.05 torr, more preferably from 200° C. to 250° C. and 0.01 torr to 0.05 torr. The distillation apparatus (11) can be any high-vacuum design including, but not limited to, a short path evaporator, wiped-film evaporator, centrifugal molecular still, or falling film evaporator.

Steps (a)–(c) of the present invention produce a tocol blend in an efficient and economical manner using a minimum number of steps. One advantage of the present invention is that prior to the heating step (a), an alcohol is not added to the first tocol admixture. Because extraneous substances such as solvents and alcohols are not added to the first tocol admixture, an additional step to remove these substances is not required. Additionally, the tocol concentration of the fourth tocol admixture is higher when compared to the tocol concentration of other compositions that were produced by other prior art techniques. The amount of tocols present in the fourth tocol admixture can vary depending upon the source of the first tocol admixture and the concentration of the tocols in the first tocol admixture. In a different embodiment, the fourth tocol admixture has a tocol concentration of from 1 to 50%, 5 to 45%, 10 to 40%, 15 to 35%, or 20 to 30% by weight tocols. In another embodiment, the fourth tocol admixture has a tocol concentration of from 8 to 30% by weight tocols. In one embodiment, the fourth tocol admixture has a tocol concentration of from 45 to 50% by weight tocols. The overall recovery of the tocols from steps (a)–(c) described above is generally from 72% to 97%, more typically from 75% to 92%, more typically from 80% to 85%.

Typically, the fourth tocol admixture comprises a non-tocol component. The non-tocol component can vary depending upon the source of the first tocol admixture. Examples of non-tocol components include, but are not limited to, hydrocarbons, diglycerides, and/or unreacted sterols.

In one embodiment, the heating and distillation steps can be accomplished in batch, semi-batch, or continuous modes of operation, preferably a continuous mode. The distillation steps are conducted in series.

Methods for Separating Tocotrienols and Tocols from a Tocol-Containing Mixture

Once the fourth tocol admixture has been produced, the fourth tocol admixture is subjected to an extraction step in order to separate the tocotrienols or tocols from the fourth tocol admixture. Extraction techniques that can be used in the present invention include, but are not limited to, single contact extraction (i.e., batch), simple multistage contact extraction, countercurrent multistage extraction, true continuous countercurrent extraction, or continuous countercurrent extraction. Any of the extraction techniques disclosed in Perry et al., Chemical Engineers' Handbook, $5^{th}$ Edition (McGraw-Hill, 1973), and Lo et al., Handbook of Solvent Extraction, Reprint Edition (Krieger, 1991), which are herein incorporated by reference in their entirety, can be used in the present invention. In a preferred embodiment, the extraction step is a continuous countercurrent extraction.

Countercurrent extraction equipment useful in the present invention include, but are not limited to, columns (agitated and non-agitated), mixer-settlers, or centrifugal extractors. Examples of agitated columns include, but are not limited to, the Karr reciprocating plate, rotating disc, asymmetric disc, Kuhni, York-Scheibel, and the Oldshue-Rushton. Examples of non-agitated columns include, but are not limited to, spray plate, baffle plate, packed plate, and perforated plate. Examples of centrifugal extractors include, but are not limited to, those produced by Robatel Inc., Pittsfield, Mass.; Westfalia Separator Inc., Northvale, N.J.; and Baker Perkins Inc. (Podbielniak), Saginaw, Mich.

In a preferable embodiment, the fourth tocol admixture and the extraction solvent are semi-continuously or continuously charged to the extractor, preferably continuously. The fourth tocol admixture and the extraction solvent are intimately contacted in the extractor where they flow countercurrently to one another. In one embodiment, when the extraction solvent further comprises a co-solvent, the extraction process is performed in a continuous countercurrent unit, where extraction solvent and co-solvent are charged to opposite ends of the extractor. The fourth tocol admixture physically enters the extractor between the extraction solvent and co-solvent. The batch, semi-continuous, or continuous extractions may be performed over a range of temperatures and pressures. The extraction temperature must remain between the freezing and boiling points of the extracting solvent, and below the temperature at which the tocotrienols and tocols begin to thermally degrade.

When the fourth tocol admixture is contacted with the extraction solvent, a two-phase system is produced comprising a first phase and a second phase. Typically the first phase comprises the majority (i.e., greater than 50% but typically greater than 90% or even 95%) or super majority of the extraction solvent; however, a small amount of the extraction solvent may dissolve in the second phase depending upon the type and amount of extraction solvent that is selected. The second phase is generally the raffinate, which comprises the non-tocol components. Additionally, the majority of the tocols and tocotrienols initially present in the fourth tocol admixture are present in the first phase; however, a small amount of tocols and tocotrienols may also be present in the second phase, which varies depending upon the extraction solvent and technique employed.

In one embodiment, the extraction step can be conducted in a plurality of theoretical stages. In one embodiment, the number of theoretical stages is greater than one, typically from 2 to 50, and preferably from 2 to 7. In a typical extraction process of the present invention, after the fourth tocol admixture is agitated with the extraction solvent, the resultant mixture is allowed to separate into two phases. The density of the extraction solvent relative to the fourth tocol admixture determines if the first phase is the top or bottom phase. In one embodiment, the first phase is the top phase and the second phase is the bottom phase. In one embodiment, the first phase, which contains the separated tocols or tocotrienols, is removed from the second phase using techniques known in the art. The second phase can then be extracted again with fresh extraction solvent in order to separate any remaining tocols or tocotrienols that were not extracted in the previous extraction step.

Once the first phase has been removed from the second phase, the extraction solvent can be removed from the first phase in order to isolate the tocotrienols or tocols. In one embodiment, the extraction solvent is evaporated or distilled from the first phase. In an alternative embodiment, the first phase can be cooled to induce the crystallization of wax present in the first phase. The temperature at which the first phase is cooled depends upon the extraction solvent used. The first phase is typically cooled to −10 to 35° C., preferably from 20 to 25° C. The first phase is then filtered in order to remove the wax.

The temperature at which the extraction step is performed can vary depending upon the tocotrienols and tocols present in the fourth tocol admixture. The temperature is typically determined by the degradation temperature of the tocotrienols or tocols and the residence time. In one embodiment, a thermal gradient may be applied across the extraction column. For example, the top of the extraction column may be maintained at a different temperature than the bottom of the extraction column. In one embodiment, the temperature is from 0 to 100° C., preferably from 20 to 55° C., and even more preferably from 40 to 55° C. The residence time of the extraction can vary from 10 seconds to 10 hours depending upon the extraction solvent and the extraction equipment used.

The extraction solvent employed in the extraction step (d) may be selected from a variety of organic solvents that are miscible with water and are more polar in nature than the non-tocol component present in the fourth tocol admixture. Generally, the extraction solvent should satisfy four requirements: (1) it should form a second liquid phase at equilibrium when contacted with the fourth tocol admixture; (2) it should have a higher selectivity for dissolving the tocotrienols or tocols than the other components in the fourth tocol admixture; (3) it should have characteristics that enable it to be separated from the tocotrienols or tocols by evaporation, distillation, crystallization, or some other separation operation; and (4) it should be inert with respect to the tocotrienols and tocols.

The majority of polar, organic solvents that are miscible with water known in the art can be used as the extraction solvent of the present invention for separating tocotrienols and tocols from a tocol-containing mixture. In one embodiment, the extraction solvent is an aqueous composition. In another embodiment, the extraction solvent does not comprise an alcohol. Examples of extraction solvents useful for separating tocotrienols and tocols from a tocol mixture include, but are not limited to, acetic acid, aqueous acetic acid, propionic acid, aqueous propionic acid, acetone, aqueous acetone, 1,4-dioxane, aqueous 1,4-dioxane, dimethylacetamide, aqueous dimethylacetamide, dimethylformamide, aqueous dimethylformamide, N-methyl pyrrolidinone, aqueous N-methyl pyrrolidinone, butadiene sulfone, aqueous butadiene sulfone, dimethyl sulfoxide, aqueous dimethyl sulfoxide, 2-methoxyethyl ether, aqueous 2-methoxyethyl ether, dimethoxyethane, aqueous dimethoxyethane, aqueous methanol, aqueous ethanol, aqueous 2-methoxyethanol, aqueous 2-ethoxyethanol, aqueous 2-propoxyethanol or a combination thereof. In a preferred embodiment, the extraction solvent comprises acetic acid, aqueous acetic acid, propionic acid, aqueous propionic acid, aqueous acetone, aqueous acetonitrile, aqueous 1,4-dioxane, aqueous dimethylacetamide, aqueous dimethylformamide, or a combination thereof.

The amount of extraction solvent that is needed to separate the tocotrienols or tocols from the fourth tocol admixture varies depending upon the amount of the fourth tocol admixture and the extraction equipment that is used. Typically, enough extraction solvent must be used in order to produce two phases. The number of theoretical stages used and the temperature at which the extraction is preformed also determine the amount of extraction solvent used. In one embodiment, the extraction solvent/fourth tocol admixture ratio is from 100:1 to 1:100, preferably from 20:1 to 1:20.

The use of neat alcohols as the extraction solvent is not a feature of the present invention. When the extraction solvent is neat alcohol, it is difficult to achieve phase separation between the extraction solvent and the raffinate. However, the present invention does not exclude the use of an alcohol in combination with other co-solvents. Examples of co-solvents useful in the present invention include, but are not limited to a hydrocarbon solvent or water. The co-solvent can be partially or fully miscible with the extraction solvent, or it can be completely immiscible with the extraction solvent. The co-solvent can be mixed with the extraction solvent prior to the extraction step, or the co-solvent and the extraction solvent can extract the fourth tocol admixture in a continuous manner. In one embodiment, when water is the co-solvent, the water is mixed with the extraction solvent prior to the extraction step.

A "hydrocarbon solvent" is defined herein as any solvent that is composed of non-polar components that promote the formation of a second immiscible liquid phase with the extraction solvent. The hydrocarbon solvent can be halogenated or unhalogenated. The amount of hydrocarbon solvent that can be used can vary depending upon the extraction equipment used and the desired separation. In one embodiment, the extraction solvent/hydrocarbon solvent ratio is from 20:1 to 1:20.

The hydrocarbon solvent typically comprises a straight or branched $C_5$ to $C_{30}$ alkane, a straight or branched $C_5$ to $C_{30}$ alkene, an aromatic compound, or a combination thereof. The hydrocarbon solvent preferably comprises heptane, benzene, toluene, or a combination thereof. In a preferred embodiment, the hydrocarbon solvent comprises heptane or toluene. In another embodiment, the hydrocarbon solvent comprises xylene, methylene chloride, carbon tetrachloride, ethylene dichloride, monochlorobenzene, trichloroethylene, trichloroethane, or a combination thereof. Additionally, any hydrocarbons that are native to vegetable oils, such as squalene, can be used as the hydrocarbon solvent.

The present invention can be used to selectively separate particular types of tocotrienols from a tocol admixture, wherein the tocol admixture contains at least one tocopherol. In one embodiment, the present invention can selectively separate gamma-tocotrienol from a tocol-containing mixture comprising alpha-tocopherol. By selecting the appropriate extraction solvent, it is possible to tailor the extraction in order to selectively separate particular types of tocotrienols. When gamma-tocotrienol is separated from the tocol mixture, the extraction solvent preferably comprises aqueous acetone. In a more preferred embodiment, the aqueous acetone comprises from 15 to 30% by weight water and from 70 to 85% by weight acetone, wherein the sum of the acetone and water is equal to 100%. In a more preferred embodiment, the aqueous acetone comprises from 20 to 26% by weight water and from 74 to 80% by weight acetone, wherein the sum of the acetone and water is equal to 100%.

Any of the co-solvents listed above may be added to the extraction solvent in order to enhance or increase the separation of the tocotrienol from the tocol mixture.

For example, a hydrocarbon solvent or water can be used in combination with the extraction solvent.

In another preferred embodiment, when gamma-tocotrienol is separated from a tocol-containing mixture, (1) the first tocol admixture that is used is rice bran oil deodorizer distillate; (2) the extraction solvent is aqueous acetone comprising 74 to 80% by weight acetone and from 20 to 26% by weight water, and (3) the extraction step is continuous and countercurrent.

In another embodiment, when tocotrienol is separated from a tocol-containing mixture, the extraction solvent comprises aqueous acetonitrile, and the aqueous acetonitrile comprises from 5 to 25% by weight water and from 75 to 95% by weight acetonitrile, wherein the sum of the acetonitrile and water is equal to 100%. In a preferred embodiment, when gamma-tocotrienol is separated from a tocol-containing mixture, (1) the first tocol admixture that is used is palm oil deodorizer distillate; (2) the extraction solvent is aqueous acetonitrile comprising 75 to 95% by weight acetonitrile and from 5 to 25% by weight water, and (3) the extraction step is batch or continuous and countercurrent.

In another embodiment, when tocotrienol is separated from a tocol-containing mixture, the extraction solvent comprises aqueous acetic acid, and the aqueous acetic acid comprises from 5 to 15% by weight water and from 85 to 95% by weight acetic acid, wherein the sum of the acetic acid and water is equal to 100%. In another embodiment, the extraction solvent comprises neat acetic acid.

In another embodiment, when tocotrienol is separated from a tocol-containing mixture, the extraction solvent comprises aqueous propionic acid, and the aqueous propionic acid comprises from 21 to 30% by weight water and from 70 to 79% by weight propionic acid, wherein the sum of the propionic acid and water is equal to 100%.

In another embodiment, when tocotrienol is separated from a tocol-containing mixture, the extraction solvent comprises aqueous methanol, and the aqueous methanol comprises from 7 to 15% by weight water and from 85 to 93% by weight methanol, wherein the sum of the methanol and water is equal to 100%.

In another embodiment, when tocotrienol is separated from a tocol-containing mixture, the extraction solvent comprises aqueous ethanol, and the aqueous ethanol comprises from 17 to 30% by weight water and from 70 to 83% by weight ethanol, wherein the sum of the ethanol and water is equal to 100%.

In another embodiment, when tocotrienol is separated from a tocol-containing mixture, the extraction solvent comprises aqueous isopropanol, and the aqueous isopropanol comprises from 25 to 40% by weight water and from 60 to 75% by weight isopropanol, wherein the sum of the isopropanol and water is equal to 100%.

In another embodiment, when tocotrienol is separated from a tocol-containing mixture, the extraction solvent comprises aqueous 2-methoxyethanol, and the aqueous 2-methoxyethanol comprises from 5 to 20% by weight water and from 80 to 95% by weight 2-methoxyethanol, wherein the sum of the 2-methoxyethanol and water is equal to 100%.

Not wishing to be bound by theory, it is believed that the majority of the tocotrienols are soluble in the extraction solvent of the present invention (first phase), but only a small amount of the tocopherols are soluble. The tocopherols are soluble in the hydrocarbon phase (second phase). The distribution of the tocopherols between the first phase and the second phase can depend upon the fraction of water in the extraction solvent. By increasing the amount of water present in the extraction solvent, the tocopherol is driven into the second phase while the tocotrienol remains in the first phase.

In an alternative embodiment, once the fourth tocol admixture has been extracted with the extraction solvent to remove tocotrienol(s) from the admixture, the second phase (raffinate phase) can be extracted with a second phase extraction solvent of the present invention in order to increase the tocopherol concentration. In one embodiment, the process comprises removing the first phase from the second phase in step (d), extracting the second phase with a second phase extraction solvent comprising a polar organic solvent that is miscible with water to produce a two phase system comprising a third phase containing the majority of the second phase extraction solvent and a fourth phase, wherein the selectivity of the second extraction solvent for the tocopherol with respect to the non-tocol component is greater than unity, and removing the third phase from the fourth phase, with the proviso that the second phase extraction solvent is not a neat alcohol. In a preferred embodiment, the tocopherol is alpha-tocopherol.

Typically, the second phase extraction solvent can be any of the extraction solvents listed above. Generally, the second phase extraction solvent is different than the extraction solvent used to separate the tocotrienol(s) from the tocopherol(s) in the fourth tocol admixture. When the second phase extraction solvent is the same as the extraction solvent, the amount of the second phase extraction solvent used to extract the tocopherol(s) from the second phase is typically not the same as the amount of extraction solvent that is used to extract the tocotrienol(s) from the fourth tocol admixture. For example, a different amount of a co-solvent such as hydrocarbon solvent or water can be added to the second phase extraction solvent relative to the extraction solvent in order to separate the tocopherol(s) from the second phase. In one embodiment, the second phase extraction solvent comprises aqueous acetone comprising from 81 to 93% by weight acetone and from 7 to 19% by weight water, wherein the sum of the acetone and water is equal to 100%. In a preferred embodiment, the aqueous acetone is 83 to 87% acetone and 13 to 17% by weight water.

In a preferred embodiment, when alpha-tocopherol is separated from the tocol-containing mixture that has already been extracted a first time to separate gamma-tocotrienol from the fourth tocol admixture, (1) the first tocol admixture comprises once bran oil deodorizer distillate; (2) the second phase extraction solvent comprises aqueous acetone comprising 85% by weight acetone and from 15% by weight water, and (3) the extraction step is continuous and countercurrent.

In another embodiment, the fourth tocol admixture is extracted with an extraction solvent of the present invention to selectively separate the tocols from the fourth tocol admixture. Any of the extraction solvents described above for separating tocotrienol(s) from a tocol mixture can be used to separate tocol from a tocol mixture. In one embodiment, the extraction solvent comprises an aqueous composition. In one embodiment, the extraction solvent does not comprise a neat alcohol. In a preferred embodiment, the extraction solvent comprises aqueous acetone. In a preferred embodiment, aqueous acetone comprises from 70 to 98%, preferably 75 to 93%, and more preferably from 83 to 88% by weight acetone and from 2 to 30%, preferably 7 to 25%, and more preferably from 12 to 17% by weight water, wherein the sum of the acetone and water is equal to 100%. In another embodiment, the aqueous acetone comprises from 70 to 85%, preferably from 74 to 80% by weight acetone and from 15 to 30%, preferably from 20 to 26% by weight water, wherein the sum of the acetone and water is equal to 100%.

Any of the co-solvents listed above may be added to the extraction solvent in order to enhance or increase the separation of the tocol from the tocol mixture. For example, a hydrocarbon solvent or water can be used in combination with the extraction solvent. In one embodiment, the extraction solvent comprises aqueous acetone and the hydrocarbon solvent comprises heptane. In another embodiment, the extraction solvent comprises methanol and the hydrocarbon solvent comprises heptane.

In a preferred embodiment, when tocols are separated from the a tocol-containing mixture, (1) the first tocol admixture comprises rice bran oil deodorizer distillate; (2) the extraction solvent comprises aqueous acetone comprising 70 to 98% by weight acetone and from 2 to 30% by weight water, and (3) the extraction step is continuous and countercurrent.

Alternatively, once the tocols have been separated from the fourth tocol admixture after extraction step (d), the resultant tocol mixture can be further extracted with a third extraction solvent of the present invention in order to selectively separate tocotrienol(s) from the tocol mixture. In one embodiment, the process comprises extracting tocotrienol from the first phase produced after step (d) with a third extraction solvent comprising a polar, organic solvent that is miscible with water to produce a two phase system comprising a third phase containing the majority of the third extraction solvent and a fourth phase, wherein the selectivity of the third extraction solvent for the tocotrienol with respect to the tocopherol is greater than unity, and removing the third phase from the fourth phase, with the proviso that the third extraction solvent is not a neat alcohol. The type and amount of third extraction solvent required to separate the tocotrienol from the tocol mixture will depend upon the amount of hydrocarbon solvent present in the tocol mixture as well as the particular type of tocotrienol that is being separated. Any of the extraction solvents listed above can be used as the third extraction solvent. Preferably, the tocotrienol is gamma-tocotrienol.

The extraction solvent of the present invention selectively removes tocotrienols, tocopherols, or tocols from a tocol-containing mixture. The term "selectivity" as referred to herein can be used to quantify the efficiency of the extraction step of the present invention with respect to the separation of the tocotrienol, tocopherol, or the tocol from the tocol-containing mixture. For example, the selectivity of tocotrienol relative to tocopherols is defined in equation I;

$$\text{selectivity of tocotrienol with respect to tocopherol} = \frac{\text{distribution coefficient of tocotrienols}}{\text{distribution coefficient of tocopherols}} \quad (I)$$

wherein the distribution coefficient for the tocotrienols and the tocopherols can be calculated using equations II and III, respectively:

$$\text{distribution coefficient of tocotrienols} = \frac{\text{weight \% tocotrienols (first phase)}}{\text{weight \% tocotrienols (second phase)}} \quad (II)$$

$$\text{distribution coefficient of tocopherols} = \frac{\text{weight \% tocopherols (first phase)}}{\text{weight \% tocopherols (second phase)}} \quad (III)$$

The selectivity of the tocols with respect to the non-tocol component can be calculated by equation IV:

$$\text{selectivity of tocols with respect to the non-tocol component} = \quad (IV)$$

$$\text{distribution coefficient of tocols} \over \text{distribution coefficient of non-tocol component}$$

wherein the distribution coefficient of the tocols and non-tocol component can be calculated using equations V and VI, respectively:

$$\text{distribution coefficient of tocols} = \frac{\text{weight \% tocols (first phase)}}{\text{weight \% tocols (second phase)}} \quad (V)$$

$$\text{distribution coefficient of non-tocol component} = \quad (VI)$$

$$\frac{\text{weight \% non-tocol component (first phase)}}{\text{weight \% non-tocol component (second phase)}}$$

The distribution coefficient of the non-tocol component can be determined using techniques known in the art, and will vary depending upon the composition of the raffinate (second phase).

The selectivity of tocopherols with respect to the non-tocol component can be calculated by equation VII:

$$\text{selectivity of tocopherols with respect to non-tocol component} = \quad (VII)$$

$$\frac{\text{distribution coefficient of tocopherols}}{\text{distribution coefficient of non-tocol component}}$$

wherein the distribution coefficient for the tocopherols and the non-tocol component can be calculated using equations VIII and IX, respectively:

$$\text{distribution coefficient of tocopherols} = \quad (VIII)$$

$$\frac{\text{weight \% tocopherols (first phase)}}{\text{weight \% tocopherols (second phase)}}$$

$$\text{distribution coefficient of non-tocol component} = \quad (IX)$$

$$\frac{\text{weight \% non-tocol component (first phase)}}{\text{weight \% non-tocol component (second phase)}}$$

When countercurrent extraction techniques (non-equilibrium) are used to extract the fourth tocol admixture, the selectivity of the extraction, using the selectivity of the extraction solvent for the tocotrienol relative to the tocopherol as an example, can be calculated from equation X:

$$\text{modified selectivity} = \frac{\text{(sum tocotrienol in first phase)}/\text{(sum tocotrienol in second phase)}}{\text{(sum tocopherol in first phase)}/\text{(sum tocopherol in second phase)}} \quad (X)$$

Other modified selectivities can be similarly calculated using equation X above.

In one embodiment, the selectivity of the extraction step is greater than one. The upper limit of the extraction selectivity can in theory approach infinity, and is dependent upon the distribution coefficients of the tocotrienols, tocopherols, tocols, and the non-tocol component. In various embodiments, the extraction selectivity is from greater than 1, 1.5, 2, 3, or 5 to 5, 10, 15, 20, 40, 50, 60, 70, 80, or 90.

Compositions of Matter

The invention further relates to tocotrienol-containing compositions produced by the present invention. In a preferred embodiment, the composition comprises a high concentration of tocotrienols. In one embodiment, the composition comprises gamma-tocotrienol and alpha-tocopherol, wherein the ratio gamma-tocotrienol to alpha-tocopherol is from 1:1 to 10:1. In one embodiment, the composition comprises gamma-tocotrienol and alpha-tocopherol, wherein the ratio gamma-tocotrienol to alpha-tocopherol is 9:1, 8:1, 7:1, 6:1, 5:1, 4:1, 3:1, or 2:1. In another embodiment, the composition comprises gamma-tocotrienol, wherein the gamma-tocotrienol is from 4 to 20%, preferably from 4.5 to 17.0% by weight of the composition.

EXAMPLES

The following examples are put forth so as to provide those of ordinary skill in the art with a complete disclosure and description of how the methods claimed herein are evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at ambient temperature and pressure is at or near atmospheric.

Example 1

Rice bran oil deodorizer distillate was esterified and distilled as described in U.S. Pat. No. 5,660,691 to Barnicki et al. to produce the fourth tocol admixture. A 500 kg batch of first tocol admixture was heated at 170° C. for 14 hours at 50 mmHg initially, and the pressure was reduced to 30 mmHg at the end of the heating step. During the heating step, the reaction was sparged with nitrogen at 100 SCF/hr. The resultant mixture is the second tocol admixture.

A one-inch diameter glass distillation column was equipped with a vacuum pump, refluxing distillation head, reflux ratio controller, metered feed pump, heated feed line, heated feed tank, and collection vessels for the distillate and bottoms product. The column was composed of a rectification section containing six inches of structured packing, a stripping section containing 18 inches of structured packing, and a reboiler section containing twelve inches of ⅛ inch spherical glass beads. The reboiler was fitted with a brass block heater, and the rectification and stripping sections were wrapped with heat tape and insulated.

The second tocol admixture was fed continuously to the column at a rate of 300 mL/hr, while the reboiler temperature was from 240 to 315° C. and the reflux ratio was from 0.33 to 2.00. The pressure at the top of the column was maintained at 0.7 torr and all column heat tapes at 220° C. At each reboiler temperature and reflux ratio setting the column was allowed to come to equilibrium. The bottoms of this distillation step is the third tocol admixture.

The third tocol admixture was fed continuously at a rate of 400 mL/hr to a single-staged 6-inch wiped film still equipped with a heating mantle, feed pump, high vacuum pump, and distillate and residue receivers. The still was maintained at a pressure of 0.1 torr and a temperature of 240° C., or alternatively 50 microns and 220° C. This distillate, which is the fourth tocol admixture, is composed of 11.4% tocols.

The fourth tocol admixture was held in a jacketed feed tank at 51° C. and was fed to the top of a continuous countercurrent extraction apparatus at a rate of 1.2 mL/min. The continuous countercurrent extraction apparatus was a 45-inch by ½-inch fully jacketed column agitated by 45 Teflon plates spaced at one-inch intervals along the column. The plates reciprocated with a total travel length of 0.5 inches to mimick a Karr reciprocating plate. The extraction apparatus was calculated to operate at 2 to 7 theoretical stages. The solvent mixture, which was 75% acetone and 25% water, was fed into the bottom at a rate of 12 mL/min. The temperature was maintained at 51° C. by circulation of water through the column jacket. The waxes (raffinate), which were depleted in tocols, were taken from the bottom of the column while the solvent containing tocols was allowed to overflow the top. The residence time of material in the extraction column was around 15 minutes, which is the time the extraction solvent enters the extraction column to the time the extraction solvent exits the extraction column. The overflow tank was emptied and the underflow was completely drained at 15-minute intervals. The compositions of the product and the raffinate were found to be constant after two drainings. The solvent was evaporated and the samples were dried before analysis. The samples were analyzed by liquid chromatography (detection limit of 0.1%) for weight % tocols. The results are listed in Table 1. Table 2 shows the amount of each tocol as a fraction of the total tocols in the mixture. The amount of alpha-tocotrienol in these samples was below the analytical detection limit. The selectivity of gamma-tocotrienol with respect to alphatocopherol for Examples 1–36 is shown in Table 19.

Example 2

The procedure of Example 1 was followed except that 80% acetone and 20% water was used as the solvent.

Example 3

The procedure of Example 1 was followed except that 85% acetone and 15% water was used as the solvent.

Example 4

The procedure of Example 1 was followed except that 70% acetone and 30% water was used as the solvent.

Example 5

The procedure of Example 1 was followed except that the fourth tocol admixture was composed of 8.8% total tocols.

Example 6

The procedure of Example 1 was followed except that the fourth tocol admixture was composed of 18.3% total tocols. The overflow tank was emptied at 10-minute intervals.

Example 7

The raffinate (second phase) from Example 5 was extracted with a second extraction solvent composed of 85% acetone and 15% water. The raffinate from Example 5 was composed of 0.3% gamma-tocotrienol, 0.9% gamma-tocopherol, and 2.4% alpha tocopherol (3.6% total tocols). Extraction of a 15 g sample of raffinate with the second extraction solvent produced a third phase containing 3.9 g of tocols composed of 1.6% gamma-tocotrienol, 0.3% delta-tocopherol, 4.1% gamma-tocopherol, and 9.5% alpha-tocopherol (15.5% total tocols). The raffinate (fourth phase) from this extraction (11.1 g) contained only 0.2% total tocols. The net result of the two continuous extractions is that a fourth tocol admixture composed of 0.3% delta-tocotrienol, 3.9% gamma-tocotrienol, 0.2% delta-tocopherol, 1.6% gamma-tocopherol, and 2.8% alpha-tocopherol (8.8% total tocols) was separated into two fractions having different relative amounts of tocols. After the first extraction, the first phase rich in gamma-tocotrienol contained 1.7% delta-tocotrienol, 17.0% gamma-tocotrienol, 0.5% delta-tocopherol, 4.2% gamma-tocopherol, and 4.4% alpha-tocopherol. After the second extraction of the second phase, the third phase rich in alpha-tocopherol contained 1.6% gamma-tocotrienol, 0.3% delta-tocopherol, 4.1% gamma-tocopherol, and 9.5% alpha-tocopherol. These results are summarized in Table 3. This example demonstrates that it is possible selectively increase the concentration of gamma-tocotrienol and alpha-tocopherol by using a process of the present invention.

TABLE 1

Concentration of Gamma-Tocotrienol by Extraction of Initial Tocol Concentrates With Aqueous Acetone Containing Varied Amounts of Water

| Example No. | Solvent (fraction acetone) | Phase[a] | Weight (g) | Total Tocols (g) | delta Tocotrienol (g) | gamma Tocotrienol (g) | delta Tocopherol (g) | gamma Tocopherol (g) | alpha Tocopherol (g) |
|---|---|---|---|---|---|---|---|---|---|
| 1 | 0.75 | top | 3.2 | 1.1 | 0.1 | 0.6 | 0.0 | 0.2 | 0.2 |
|  |  | bottom | 13.6 | 1.0 | 0.0 | 0.1 | 0.0 | 0.2 | 0.7 |
| 2 | 0.80 | top | 5.0 | 1.7 | 0.1 | 0.7 | 0.1 | 0.3 | 0.5 |
|  |  | bottom | 9.6 | 0.3 | 0.0 | 0.0 | 0.0 | 0.0 | 0.3 |
| 3 | 0.85 | top | 8.2 | 2.0 | 0.1 | 0.7 | 0.1 | 0.4 | 0.8 |
|  |  | bottom | 6.7 | 0.0 | 0.0 | 0.0 | 0.0 | 0.0 | 0.0 |
| 4 | 0.70 | top | 1.9 | 0.6 | 0.0 | 0.3 | 0.0 | 0.1 | 0.1 |
|  |  | bottom | 7.7 | 0.5 | 0.0 | 0.1 | 0.0 | 0.1 | 0.3 |
| 5 | 0.75 | top | 3.2 | 0.9 | 0.1 | 0.5 | 0.0 | 0.1 | 0.1 |
|  |  | bottom | 13.7 | 0.5 | 0.0 | 0.0 | 0.0 | 0.1 | 0.3 |

TABLE 1-continued

Concentration of Gamma-Tocotrienol by Extraction of Initial Tocol Concentrates With Aqueous Acetone Containing Varied Amounts of Water

| Example No. | Solvent (fraction acetone) | Phase[a] | Weight (g) | Total Tocols (g) | delta Tocotrienol (g) | gamma Tocotrienol (g) | delta Tocopherol (g) | gamma Tocopherol (g) | alpha Tocopherol (g) |
|---|---|---|---|---|---|---|---|---|---|
| 6 | 0.75 | top | 4.9 | 1.4 | 0.1 | 0.7 | 0.0 | 0.2 | 0.3 |
|  |  | bottom | 5.7 | 0.4 | 0.0 | 0.0 | 0.0 | 0.1 | 0.3 |

[a]The top phase is the first phase and the bottom phase is the second phase.

TABLE 2

The Amount of Tocol as a Fraction of the Total Tocols in the Mixture

| Example No. | Solvent (fraction acetone) | Phase[e] | delta Tocotrienol (% by wt) | gamma Tocotrienol (% by wt) (% increase[d]) | delta Tocopherol (% by wt) | gamma Tocopherol (% by wt) | alpha Tocopherol (% by wt) |
|---|---|---|---|---|---|---|---|
| 1 | 0.75 | top | 7 | 54 (1,250) | 4 | 15 | 21 |
|  |  | bottom | 1 | 9 | 3 | 21 | 67 |
| 2 | 0.80 | top | 5 | 42 (950) | 4 | 18 | 31 |
|  |  | bottom | 0 | 1 | 0 | 9 | 90 |
| 3 | 0.85 | top | 4 | 34 (750) | 3 | 18 | 41 |
|  |  | bottom | 0 | 0 | 22 | 0 | 78 |
| 4 | 0.70 | top | 8 | 55 (1,275) | 3 | 14 | 20 |
|  |  | bottom | 1 | 11 | 3 | 19 | 66 |
| fourth tocol admixture[a] | — | — | 0 | 4 | 0 | 2 | 5 |
| 5 | 0.75 | top | 6 | 61 (1,425) | 2 | 15 | 16 |
|  |  | bottom | 0 | 7 | 1 | 24 | 67 |
| fourth tocol admixture[b] | — | — | 0 | 4 | 0 | 2 | 3 |
| 6 | 0.75 | top | 9 | 52 (477) | 2 | 14 | 23 |
|  |  | bottom | 0 | 3 | 1 | 17 | 80 |
| fourth tocol admixture[c] | — | — | 1 | 9 | 0 | 3 | 6 |

[a]The fourth tocol admixture for Examples 1–4, wherein the amount of tocols present in the fourth tocol admixture is 11.4% by weight.
[b]The fourth tocol admixture for Example 5, wherein the amount of tocols present in the fourth tocol admixture is 8.6% by weight.
[c]The fourth tocol admixture for Example 6, wherein the amount of tocols present in the fourth tocol admixture is 18.3% by weight.
[d]The percent increase is measured as the increase in concentration of gamma-tocotrienol in the top phase relative to the concentration of gamma-tocotrienol in the corresponding fourth tocol admixture.
[e]The top phase is the first phase and the bottom phase is the second phase.

TABLE 3

Separation of Initial Concentrate Into Fractions Rich in Gamma-Tocotrienol and Rich in Alpha-Tocopherol

| Fraction | Extraction Solvent | delta Tocotrienol (Wt. %) | gamma Tocotrienol (Wt. %) | delta Tocopherol (Wt. %) | gamma Tocopherol (Wt. %) | alpha Tocopherol (Wt. %) | TOTAL TOCOLS (wt. %) |
|---|---|---|---|---|---|---|---|
| Feed material |  | 0.3 | 3.9 | 0.2 | 1.6 | 2.8 | 8.8 |
| 1 | 75% Acetone 25% Water | 1.7 | 17.0 | 0.5 | 4.2 | 4.4 | 27.8 |
| 2 | 85% Acetone 15% Water | 0.1 | 1.6 | 0.3 | 4.1 | 9.5 | 15.5 |

Example 8

A liquid-liquid dispersion consisting of 5.410 grams of reagent grade methanol (extraction solvent), 0.634 grams of heptane (co-solvent), and 2.707 grams of the fourth tocol admixture, prepared by the method described in Example 1 (edible oil feed), was made in a 10 mL glass centrifuge tube with a conical bottom. The dispersion was intimately contacted with a vortex mixer for three minutes before the tube was transferred to a temperature bath held at 45° C. The dispersion was held at 45° C. and agitated with a magnetic stirrer for three hours. During this period, the dispersion was further agitated for three minutes with the vortex mixer at one-hour intervals to assure that liquid-liquid phase equilibrium had been achieved. The centrifuge tube was then placed in a heated centrifuge and spun for 10 minutes at 1512 times gravitational force. Each of the resulting two immiscible liquid phases were sampled and analyzed for alpha, gamma, and delta tocopherols and alpha, gamma, and delta tocotrienols. The weight percent of these components in the raffinate (second phase) was 0.00, 0.92, 0.07, 0.81, 0.38, and 0.09, respectively. The weight percent of these components in the extraction phase (first phase) were 0.00, 2.34, 0.15, 3.99, 1.36, 0.22, respectively. Therefore, the distribution coefficient for the total tocopherols and tocotrienols between the extract and raffinate phases was 0.28.

Example 9

A liquid-liquid dispersion consisting of 5.317 grams of reagent grade acetone (extraction solvent), 0.66 grams of water, 0.486 grams of heptane (co-solvent), and 1.406 grams of the fourth tocol admixture, prepared by the method described in Example 1 (edible oil feed), was made in a 10 mL glass centrifuge tube with a conical bottom. The dispersion was intimately contacted with a vortex mixer for three minutes before the tube was transferred to a temperature bath held at 45° C. The dispersion was held at 45° C. and agitated with a magnetic stirrer for three hours. During this period, the dispersion was further agitated for three minutes with the vortex mixer at one hour intervals to assure that liquid-liquid phase equilibrium had been achieved. The centrifuge tube was then placed in a heated centrifuge and spun for 10 minutes at 1512 times gravitational force, Each of the resulting two immiscible liquid phases were sampled and analyzed for alpha, gamma, and delta tocopherols and alpha, gamma, and delta tocotrienols. The weight percent of these components in the raffinate (second phase) was 0.00, 0.89, 0.07, 0.80, 0.36, 0.08, respectively. The weight percent of these components in the extraction phase (first phase) was 0.00, 1.49, 0.11, 3.21, 1.00, 0.19, respectively. Therefore, the distribution coefficient for the sum total tocopherols and tocotrienols between the extract and raffinate phases was 0.37.

Example 10

A liquid-liquid dispersion consisting of 5.853 grams of reagent grade acetone (extraction solvent), 0.692 grams of water (co-solvent), 0.338 grams of heptane (co-solvent), and 1.328 153 grams of the fourth tocol admixture, prepared by the method described in Example 1 (edible oil feed), was made in a 10 mL glass centrifuge tube with a conical bottom. The dispersion was intimately contacted with a vortex mixer for three minutes before the tube was transferred to a temperature bath held at 45° C. The dispersion was held at 45° C. and agitated with a magnetic stirrer for three hours. During this period, the dispersion was further agitated for three minutes with the vortex mixer at one-hour intervals to assure that liquid-liquid phase equilibrium had been achieved. The centrifuge tube was then placed in a heated centrifuge and spun for 10 minutes at 1512 times gravitational force. Each of the resulting two immiscible liquid phases were sampled and analyzed for alpha, gamma, and delta tocopherols and alpha, gamma, and delta tocotrienols. The weight percent of these components in the raffinate (second phase) was 0.88, 0.76, 0.05, 0.83, 0.32, 0.17, respectively. The weight percent of these components in the extraction phase (first phase) was 0.00, 1.21, 0.12, 3.44, 0.98, 0.16, respectively. Therefore, the distribution coefficient for the sum total tocopherols and tocotrienols between the extract and raffinate phases was 0.51.

Examples 11–14

To a clean 125 milliliter graduated, fully jacketed separatory funnel equipped with a mechanical stirrer and reflux condenser, was added 15.1 g of the fourth tocol admixture, prepared by the method described in Example 1 (edible oil feed) and 60 g of the extraction solvent. The resulting dispersion was vigorously agitated for 60 minutes while being held at 51° C. Stirring was stopped, and the mixture was allowed to stand for 45 minutes while the two liquid phases separated (at 51°). The raffinate (second phase), which was denser than the first phase, was comprised of mostly hydrocarbons and was dried under vacuum to a constant weight. The extraction solvent was evaporated from the first phase, and the resulting residue was dried under vacuum to constant weight. The residues from these two layers were analyzed by liquid chromatography for a weight percent of total tocols and a relative ratio of total hydrocarbons to total tocols. The extraction solvent was aqueous acetone in Examples 11–14. The results of the examples are listed in Table 4.

TABLE 4

| Example No. | Extraction Solvent[d] | Phase[e] | Phase Mass (g) | Sum Total Tocols[b] (% increase[c]) | Relative Ratio of Total Hydro- carbons | Relative Ratio of Total Tocols | Extraction Selectivity |
|---|---|---|---|---|---|---|---|
| 11 | 93% acetone | top | 9.9 | 30.2(35.4) | 43.6 | 56.4 | 5.8 |
| 11 | 93% acetone | bottom | 7.4 | 5.9 | 81.7 | 18.3 | |
| 12 | 90% acetone | top | 8.8 | 28.9(29.6) | 36.6 | 63.4 | 6.4 |

TABLE 4-continued

| Example No. | Extraction Solvent[d] | Phase[e] | Phase Mass (g) | Sum Total Tocols[b] (% increase[c]) | Relative Ratio of Total Hydro-carbons | Relative Ratio of Total Tocols | Extraction Selectivity |
|---|---|---|---|---|---|---|---|
| 12 | 90% acetone | bottom | 10.6 | 7.2 | 78.6 | 21.4 | |
| 13 | 85% acetone | top | 3.5 | 38.0(70.4) | 22.7 | 77.3 | 7.8 |
| 13 | 85% acetone | bottom | 11.6 | 11.6 | 69.7 | 30.3 | |
| 14 | 75% acetone | top | 1.4 | 53.0(137.7) | 17.7 | 82.3 | 7.8 |
| 14 | 75% acetone | bottom | 13.3 | 14.5 | 62.5 | 37.5 | |
| fourth tocol admixture[a] | — | — | — | 22.3 | 60.0 | 40.0 | — |

[a] The fourth tocol admixture prior to extraction in Examples 11–14.
[b] All values expressed in %.
[c] The percent increase is measured as the increase in concentration of gamma-tocotrienol in the top phase relative to the concentration of gamma-tocotrienol in the fourth tocol admixture.
[d] Balance of 100% extraction solvent is water.
[e] The top phase is the first phase and the bottom phase is the second phase.

Examples 15–37

The fourth tocol mixture produced by the process of Example 1 was extracted with a variety of extraction solvents of the present invention in order to separate tocotrienols, particularly gamma-tocotrienol, from a tocol-containing mixture. After the extraction was complete, the extraction solvent was evaporated and the samples were dried before analysis. When the solvent is expressed in %, the remaining amount of solvent is water so that the sum of the water and solvent is 100%. The amount of δ-tocotrienol (δ-tri), γ-tocotrienol (γ-tri), α-tocotrienol (α-tri), δ-tocopherol (δ-toco), γ-tocopherol (γ-toco), β-tocopherol (β-toco), and α-tocopherol (α-toco) were determined by liquid chromatography (detection limit of 0.1%) and are expressed in weight %. The sum of the tocotrienols and tocopherols in grams is shown in Tables 5, 7, 9, 11, 13, 15, and 17 under "weight." The data in Tables 5–18 demonstrate that a variety of polar, organic solvents that are miscible with water can be used to separate tocotrienols from a tocol mixture. The selectivity of the extraction solvent for gamma-tocotrienol with respect to alpha-tocopherol for Examples 1–10, 15–22, and 24–37 can be found in Table 19.

TABLE 5

Aqueous Methanol Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 15 | 0.02 | 0.46 | — | 0.07 | 0.12 | 1.1 | 3.31 | 5.08 | bottom wax | 93% | 17.3 |
| 15 | 0.75 | 13.62 | 4.13 | 0.78 | 0.6 | 8.88 | 11.81 | 40.57 | top | methanol | 5.9 |
| 15 | 0.18 | 3.71 | 1.65 | 0.21 | 0.21 | 3.06 | 5.55 | 14.57 | feed | | |
| 16 | — | 1.77 | 0.83 | 0.13 | 0.19 | 2.35 | 4.64 | 9.91 | bottom wax | 85% | 20.8 |
| 16 | 0.91 | 12.95 | 3.95 | 0.7 | 0.45 | 5.39 | 5.89 | 30.24 | top | methanol | 3.1 |
| 16 | 0.18 | 3.39 | 1.28 | 0.2 | 0.25 | 2.75 | 4.95 | 12.82 | feed | | |

[a] The top phase is the first phase and the bottom wax is the second phase.

TABLE 6

Aqueous Methanol Extractions-% by weight tocotrienols and tocopherols in the bottom phase (first phase)

| Example | δ-tri | γ-tri | α-tri | δ-toco | β-toco | γ-toco | α-toco | total | γ-tri/α-toco |
|---|---|---|---|---|---|---|---|---|---|
| 15 | 0.75 | 13.62 | 4.13 | 0.78 | 0.6 | 8.88 | 11.81 | 40.57 | 1.2 |
| 16 | 0.91 | 12.95 | 3.95 | 0.7 | 0.45 | 5.39 | 5.89 | 30.24 | 2.2 |

TABLE 7

Aqueous 2-Methoxyethanol Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 17 | — | — | — | 0.02 | — | — | 0.14 | 0.16 | top wax | 90% | 2 |
| 17 | 0.52 | 8.56 | 2.36 | 0.51 | 0.46 | 5.35 | 6.8 | 24.56 | bottom | 2-methoxy | 7.3 |
| 17 | 0.15 | 2.56 | 0.65 | 0.17 | 0.17 | 2.03 | 3.03 | 8.76 | feed | ethanol | |

TABLE 7-continued

Aqueous 2-Methoxyethanol Extractions

| Example | δ-tri | γ-tri | α-tri | δ-toco | β-toco | γ-toco | α-toco | total | phase[a] | solvent | weight |
|---------|-------|-------|-------|--------|--------|--------|--------|-------|----------|---------|--------|
| 18 | 0.02 | 0.12 | 0.22 | — | — | 0.42 | 1.57 | 2.35 | top wax | 85% | 4.9 |
| 18 | 0.65 | 10.65 | 2.84 | 0.61 | 0.46 | 5.5 | 5.21 | 25.92 | bottom | 2-methoxy ethanol | 4.3 |
| 18 | 0.15 | 2.53 | 0.76 | 0.16 | 0.17 | 2.03 | 3.22 | 9.02 | feed | | |

[a]The bottom phase is the first phase and the top wax is the second phase.

TABLE 8

Aqueous 2-Methoxyethanol Extractions-% by weight tocotrienols and tocopherols in the bottom phase (first phase)

| Example | δ-tri | γ-tri | α-tri | δ-toco | β-toco | γ-toco | α-toco | γ-tri/α-toco | total |
|---------|-------|-------|-------|--------|--------|--------|--------|--------------|-------|
| 17 | 0.52 | 8.56 | 2.36 | 0.51 | 0.46 | 5.35 | 6.8 | 1.3 | 24.6 |
| 18 | 0.65 | 10.65 | 2.84 | 0.61 | 0.46 | 5.5 | 5.21 | 2.0 | 25.9 |

TABLE 9

Aqueous Isopropanol Extractions

| Example | δ-tri | γ-tri | α-tri | δ-toco | β-toco | γ-toco | α-toco | total | phase[a] | solvent | weight |
|---------|-------|-------|-------|--------|--------|--------|--------|-------|----------|---------|--------|
| 19 | — | 0.1 | — | — | — | 0.2 | 0.8 | 1.0 | wax | 75% | 10.2 |
| 19 | 0.4 | 7.3 | 1.5 | 0.4 | 0.4 | 4.3 | 7.2 | 21.5 | top | isopropyl alcohol | 12.8 |
| 19 | 0.2 | 4.0 | 0.9 | 0.2 | 0.2 | 2.4 | 4.3 | 12.2 | feed | | |
| 20 | — | 0.4 | 0.2 | 0.0 | 0.1 | 0.6 | 2.0 | 3.3 | wax | 70% | 16.8 |
| 20 | 0.5 | 8.5 | 1.6 | 0.5 | 0.4 | 4.6 | 6.7 | 22.8 | top | isopropyl alcohol | 10.8 |
| 20 | 0.2 | 4.0 | 0.8 | 0.2 | 0.2 | 2.4 | 4.3 | 12.0 | feed | | |
| 21 | — | 0.7 | 0.2 | 0.1 | 0.2 | 1.0 | 3.0 | 5.0 | wax | 65% | 17.3 |
| 21 | 0.7 | 11.7 | 2.1 | 0.6 | 0.5 | 5.7 | 8.2 | 29.4 | top | isopropyl alcohol | 8.6 |
| 21 | 0.2 | 4.6 | 0.9 | 0.3 | 0.2 | 2.8 | 5.1 | 14.1 | feed | | |
| 22 | 0.03 | 1.05 | 0.42 | 0.1 | 0.12 | 1.24 | 2.29 | 5.25 | bottom wax | 60% isopropyl alcohol | 29.2 |
| 22 | 0.56 | 7.8 | 2.23 | 0.51 | 0.39 | 4.45 | 4.33 | 20.27 | top | | 5.6 |
| 22 | 0.14 | 2.21 | 0.51 | 0.18 | 0.16 | 1.76 | 2.45 | 7.41 | feed | | |

[a]The top phase is the first phase and the wax is the second phase.

TABLE 10

Aqueous Isopropanol Extractions-% by weight tocotrienols and tocopherols in the top phase (first phase)

| Example | δ-tri | γ-tri | α-tri | δ-toco | β-toco | γ-toco | α-toco | γ-tri/α-toco |
|---------|-------|-------|-------|--------|--------|--------|--------|--------------|
| 19 | 0.4 | 7.3 | 1.5 | 0.4 | 0.4 | 4.3 | 7.2 | 1.0 |
| 20 | 0.5 | 8.5 | 1.6 | 0.5 | 0.4 | 4.6 | 6.7 | 1.3 |
| 21 | 0.7 | 11.7 | 2.1 | 0.6 | 0.5 | 5.7 | 8.2 | 1.4 |
| 22 | 0.56 | 7.8 | 2.23 | 0.51 | 0.39 | 4.45 | 4.33 | 1.8 |

TABLE 11

Acetic Acid Extractions

| Example | δ-tri | γ-tri | α-tri | δ-toco | β-toco | γ-toco | α-toco | total | phase[b] | solvent | weight |
|---------|-------|-------|-------|--------|--------|--------|--------|-------|----------|---------|--------|
| 23 | 0.3 | 6.0 | 1.1 | 0.2 | 0.2 | 3.2 | 5.8 | 16.8 | bottom | 100% HOAc | 16.2 |
| 23 | —[a] | —[a] | —[a] | —[a] | —[a] | —[a] | —[a] | 0.0 | wax | | |
| 23 | 0.3 | 5.2 | 1.0 | 0.2 | 0.1 | 2.8 | 5.1 | 14.6 | feed | | |
| 24 | 0.0 | 0.2 | 0.0 | 0.0 | 0.1 | 0.6 | 2.1 | 3.1 | top wax | 95% | |
| 24 | 0.6 | 10.6 | 2.4 | 0.4 | 0.4 | 5.0 | 7.8 | 27.1 | bottom | HOAc | 10.9 |
| 24 | 0.3 | 5.0 | 1.1 | 0.2 | 0.2 | 2.7 | 5.0 | 14.4 | feed | | |
| 25 | 0.0 | 1.6 | 0.6 | 0.1 | 0.1 | 1.8 | 4.4 | 8.6 | top wax | 90% | |
| 25 | 1.0 | 13.9 | 2.6 | 0.4 | 0.3 | 4.1 | 5.3 | 27.6 | bottom | HOAc | 3.9 |
| 25 | 0.3 | 5.1 | 1.1 | 0.2 | 0.2 | 2.8 | 5.1 | 14.8 | feed | | |

TABLE 11-continued

Acetic Acid Extractions

| Example | δ-tri | γ-tri | α-tri | δ-toco | β-toco | γ-toco | α-toco | total | phase[b] | solvent | weight |
|---|---|---|---|---|---|---|---|---|---|---|---|
| 26 | 0.05 | 1.01 | 0.43 | 0.09 | 0.1 | 1.08 | 1.84 | 4.6 | top wax | 85% | 29 |
| 26 | 0.41 | 4.87 | 1.79 | 0.21 | 0.15 | 1.65 | 1.63 | 10.71 | bottom | HOAc | 3.6 |
| 26 | 0.08 | 1.53 | 0.61 | 0.11 | 0.12 | 1.24 | 2.15 | 5.84 | feed | | |

[a]Amounts were not calculated.
[b]The bottom phase is the first phase and the top wax is the second phase.

TABLE 12

Acetic Acid Extractions-% by weight tocotrienols and tocopherols in the bottom phase (first phase)

| Example | δ-tri | γ-tri | α-tri | δ-toco | β-toco | γ-toco | α-toco | γ-tri/α-toco |
|---|---|---|---|---|---|---|---|---|
| 23 | 0.32 | 6 | 1.14 | 0.18 | 0.18 | 3.23 | 5.79 | 1.0 |
| 24 | 0.6 | 10.6 | 2.4 | 0.4 | 0.4 | 5.0 | 7.8 | 1.4 |
| 25 | 1.0 | 13.9 | 2.6 | 0.4 | 0.3 | 4.1 | 5.3 | 2.6 |

TABLE 13

Aqueous Acetonitrile Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 27 | | 1.2 | 0.4 | 0.2 | 0.2 | 2.1 | 4.3 | 8.3 | wax | 79% | 23.7 |
| 27 | 1.4 | 18.5 | 2.3 | 0.5 | 0.2 | 3.6 | 2.9 | 29.4 | top | acetonitrile | 3.9 |
| 27 | 0.2 | 3.9 | 0.8 | 0.2 | 0.2 | 2.4 | 4.3 | 12.1 | feed | | |
| 28 | — | 0.08 | — | — | 0.1 | 0.98 | 3.31 | 4.47 | wax | 90% | 21.9 |
| 28 | 0.7 | 12.31 | 2.11 | 0.7 | 0.54 | 5.3 | 7.08 | 28.74 | top | acetonitrile | 8.4 |
| 28 | 0.23 | 4.23 | 1.05 | 0.25 | 0.23 | 2.55 | 4.47 | 13.01 | feed | | |
| 29 | 0.02 | 1.09 | 0.47 | 0.12 | 0.15 | 1.74 | 3.01 | 6.6 | bottom wax | 75% acetonitrile | 28 |
| 29 | 0.93 | 11.81 | 2.56 | 0.41 | 0.25 | 2.82 | 1.64 | 20.42 | top | | 3.7 |
| 29 | 0.16 | 2.58 | 1.05 | 0.18 | 0.19 | 2.06 | 2.98 | 9.2 | feed | | |
| 30 | — | — | — | — | — | 0.22 | 0.95 | 1.17 | bottom wax | 95% acetonitrile | 25.6 |
| 30 | 0.44 | 7.57 | 2.55 | 0.49 | 0.48 | 5.6 | 6.88 | 24.01 | top | | 12 |
| 30 | 0.16 | 2.43 | 0.74 | 0.18 | 0.19 | 1.95 | 2.79 | 8.44 | feed | | |

[a]The top phase is the first phase and the wax is the second phase.

TABLE 14

Aqueous Acetonitrile Extractions-% by weight tocotrienols and tocopherols in the top phase (first phase)

| Example | δ-tri | γ-tri | α-tri | δ-toco | β-toco | γ-toco | α-toco | γ-tri/α-toco | total |
|---|---|---|---|---|---|---|---|---|---|
| 27 | 0.4 | 7.6 | 2.6 | 0.5 | 0.5 | 5.6 | 6.9 | 1.1 | 24.0 |
| 28 | 0.7 | 12.3 | 2.1 | 0.7 | 0.5 | 5.3 | 7.1 | 1.7 | 28.7 |
| 29 | 1.4 | 18.5 | 2.3 | 0.5 | 0.2 | 3.6 | 2.9 | 6.4 | 29.4 |
| 30 | 0.9 | 11.8 | 2.6 | 0.4 | 0.2 | 2.8 | 1.6 | 7.2 | 20.4 |

TABLE 15

Aqueous Ethanol Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 31 | — | — | — | — | — | — | 0.2 | 0.2 | wax | 90% | 10 |
| 31 | 0.4 | 7.2 | 1.6 | 0.4 | 0.4 | 4.5 | 8.4 | 22.9 | top | ethanol | 19.4 |
| 31 | 0.2 | 4.5 | 0.9 | 0.2 | 0.2 | 2.7 | 5.0 | 13.9 | feed | | |
| 32 | | 0.9 | 0.2 | 0.1 | 0.1 | 1.2 | 3.1 | 5.6 | wax | 83% | 15.8 |
| 32 | 0.7 | 11.6 | 2.6 | 0.6 | 0.5 | 5.5 | 7.7 | 29.2 | top | ethanol | 6.5 |
| 32 | 0.2 | 4.2 | 0.9 | 0.2 | 0.2 | 2.6 | 4.6 | 13.0 | feed | | |
| 33 | 0.04 | 1.4 | 0.02 | 0.1 | 0.14 | 1.52 | 3.61 | 6.8 | wax | 75% | |
| 33 | 0.82 | 12.82 | 1.92 | 0.67 | 0.44 | 5.04 | 6.24 | 28.0 | top | ethanol | 5.2 |
| 33 | 0.2 | 4.0 | 0.8 | 0.2 | 0.2 | 2.4 | 4.3 | 12.1 | feed | | |

TABLE 15-continued

Aqueous Ethanol Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 34 | 0.04 | 0.96 | 0.44 | 0.08 | 0.11 | 1.11 | 1.86 | 4.6 | bottom wax | 70% ethanol | 29.7 |
| 34 | 0.69 | 8.15 | 1.8 | 0.47 | 0.34 | 3.76 | 2.69 | 17.9 | top | | 4.5 |
| 34 | 0.14 | 2.32 | 0.9 | 0.16 | 0.16 | 1.84 | 2.64 | 8.16 | feed | | |

[a]The top phase is the first phase and the wax is the second phase.

TABLE 16

Aqueous Ethanol Extractions-% by weight tocotrienols and tocopherols in the top phase (first phase)

| Example | δ-tri | γ-tri | α-tri | δ-toco | β-toco | γ-toco | α-toco | γ-tri/α-toco | total |
|---|---|---|---|---|---|---|---|---|---|
| 31 | 0.4 | 7.2 | 1.6 | 0.4 | 0.4 | 4.5 | 8.4 | 0.9 | 22.9 |
| 32 | 0.7 | 11.6 | 2.6 | 0.6 | 0.5 | 5.5 | 7.7 | 1.5 | 29.2 |
| 33 | 0.82 | 12.82 | 1.92 | 0.67 | 0.44 | 5.04 | 6.24 | 2.1 | 28.0 |
| 34 | 0.69 | 8.15 | 1.8 | 0.47 | 0.34 | 3.76 | 2.69 | 3.0 | 17.9 |

TABLE 17

Aqueous Propionic Acid Extractions

| Example | δ-tri | γ-tri | α-tri | δ-toco | β-toco | γ-toco | α-toco | total | phase[a] | solvent | weight |
|---|---|---|---|---|---|---|---|---|---|---|---|
| 35 | — | 0.2 | 0.1 | 0.0 | 0.0 | 0.6 | 2.7 | 3.7 | top wax | 79% | |
| 35 | 0.7 | 11.3 | 2.4 | 0.5 | 0.4 | 5.0 | 6.8 | 27.0 | bottom | HOPr | 4.3 |
| 35 | 0.3 | 5.3 | 1.2 | 0.2 | 0.2 | 2.9 | 5.5 | 15.6 | feed | | |
| 36 | 0.0 | 1.6 | 0.5 | 0.1 | 0.1 | 1.7 | 4.1 | 8.1 | top wax | 74% | |
| 36 | 1.1 | 16.3 | 2.9 | 0.5 | 0.4 | 5.2 | 6.8 | 33.2 | bottom | HOPr | 3.7 |
| 36 | 0.3 | 5.3 | 1.2 | 0.2 | 0.2 | 2.9 | 5.6 | 15.7 | feed | | |
| 37 | — | 0.94 | 0.49 | 0.1 | 0.12 | 1.45 | 2.53 | 5.63 | top wax | 70% | 26.8 |
| 37 | 0.65 | 8.13 | 2.42 | 0.46 | 0.27 | 3.15 | 2.91 | 17.99 | bottom | HOPr | 4.2 |
| 37 | 0.12 | 2.4 | 0.76 | 0.17 | 0.16 | 1.94 | 3.1 | 8.65 | feed | | |

[a]The bottom phase is the first phase and the top wax is the second phase.

TABLE 18

Aqueous Propionic Acid Extractions-% by weight tocotrienols and tocopherols in the bottom phase (first phase)

| Example | δ-tri | γ-tri | α-tri | δ-toco | β-toco | γ-toco | α-toco | γ-tri/α-toco |
|---|---|---|---|---|---|---|---|---|
| 35 | 0.7 | 11.3 | 2.4 | 0.5 | 0.4 | 5.0 | 6.8 | 1.7 |
| 36 | 1.1 | 16.3 | 2.9 | 0.5 | 0.4 | 5.2 | 6.8 | 2.4 |
| 37 | 0.65 | 8.13 | 2.42 | 0.46 | 0.27 | 3.15 | 2.91 | 2.8 |

TABLE 19

Summary of Selectivities

| Ex. # | Selectivity of total tocotrienol relative to total tocopherol | Selectivity of gamma-tocotrienol relative to alpha-tocopherol | Solvent | First Phase | Second Phase | Note |
|---|---|---|---|---|---|---|
| 1 | 13.88 | 19.14 | 75% acetone | top | bottom | countercurrent |
| 2 | 87.79 | 121.94 | 80% acetone | top | bottom | countercurrent |
| 3 | infinite[a] | infinite[b] | 85% acetone | top | bottom | countercurrent |
| 4 | 12.49 | 16.5 | 70% acetone | top | bottom | countercurrent |
| 5 | 26.68 | 36.49 | 75% acetone | top | bottom | countercurrent |
| 6 | 51.09 | 60.29 | 75% acetone | top | bottom | countercurrent |
| 7 | 16.80 | 22.94 | 75% acetone | top | bottom | equilibrium |
| 8 | 1.53 | —[c] | methanol and heptane | raffinate | extract | equilibrium |

TABLE 19-continued

Summary of Selectivities

| Ex. # | Selectivity of total tocotrienol relative to total tocopherol | Selectivity of gamma-tocotrienol relative to alpha-tocopherol | Solvent | First Phase | Second Phase | Note |
|---|---|---|---|---|---|---|
| 9 | 2.13 | —[c] | acetone, water, heptane | raffinate | extract | equilibrium |
| 10 | 6.39 | infinite[b] | acetone, water, heptane | raffinate | extract | equilibrium |
| 15 | 8.03 | 8.31 | 93% methanol | top | bottom wax | equilibrium |
| 16 | 4.03 | 5.76 | 85% methanol | top | bottom wax | equilibrium |
| 17 | infinite[d] | infinite[e] | 90% 2-methoxyethanol | bottom | top wax | equilibrium |
| 18 | 6.64 | 26.74 | 85% 2-methoxyethanol | bottom | top wax | equilibrium |
| 19 | 7.48 | 8.11 | 75% isopropanol | top | wax | equilibrium |
| 20 | 3.91 | 6.34 | 70% isopropanol | top | wax | equilibrium |
| 21 | 3.65 | 6.11 | 65% isopropanol | top | wax | equilibrium |
| 22 | 2.74 | 3.93 | 60% isopropanol | top | wax | equilibrium |
| 24 | 14.00 | 14.27 | 95% acetic acid | bottom | top wax | equilibrium |
| 25 | 5.04 | 7.21 | 90% acetic acid | bottom | top wax | equilibrium |
| 26 | 4.05 | 5.44 | 85% acetic acid | bottom | top wax | equilibrium |
| 27 | 13.10 | 22.86 | 79% acetonitrile | top | wax | equilibrium |
| 28 | 60.92 | 71.94 | 90% acetonitrile | top | wax | equilibrium |
| 29 | 9.49 | 19.89 | 75% acetonitrile | top | wax | equilibrium |
| 30 | infinite[d] | infinite[e] | 95% acetonitrile | top | wax | equilibrium |
| 31 | infinite[d] | infinite[e] | 90% ethanol | top | wax | equilibrium |
| 32 | 4.26 | 5.19 | 83% ethanol | top | wax | equilibrium |
| 33 | 4.62 | 5.3 | 75% ethanol | top | wax | equilibrium |
| 34 | 3.22 | 5.87 | 70% ethanol | top | wax | equilibrium |
| 35 | 12.47 | 22.43 | 79% propionic acid | bottom | top wax | equilibrium |
| 36 | 4.50 | 6.14 | 74% propionic acid | bottom | top wax | equilibrium |
| 37 | 4.84 | 7.52 | 70% propionic acid | bottom | top wax | equilibrium |

[a]Because there were no tocotrienols detected in the second phase, the selectivity of tocotrienols with respect to tocopherols approaches infinity.
[b]Because no gamma-tocotrienol detected in the second phase, the selectivity of gamma-tocotrienol with respect to alpha-tocopherol approaches infinity.
[c]Because no alpha-tocopherol was detected in the fourth tocol admixture, the selectivity of gamma-tocotrienol with respect to alpha-tocopherol cannot be calculated.
[d]Because there were no tocotrienols detected in the second phase, the selectivity of tocotrienols with respect to tocopherols approaches infinity.
[e]Because there was no gamma-tocotrienol detected in the second phase, the selectivity of gamma-tocotrienol with respect to alpha-tocopherol approaches infinity.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A method for separating a tocol from a first tocol admixture comprising at least one tocol, a first fatty acid, and an esterifying compound, comprising (a) heating the first tocol admixture comprising the tocol, the first fatty acid, and the esterifying compound for a sufficient time and temperature to substantially esterify the first fatty acid with the esterifying compound to produce a second tocol admixture comprising the tocol, esterified first fatty acid, and unesterified first fatty acid;

(b) distilling the second tocol admixture for a sufficient time and temperature to substantially remove the unesterified first fatty acid from the second tocol admixture to produce a third tocol admixture comprising the tocol and esterified fatty acid with substantially removed unesterified ed first fatty acid;

(c) distilling the third tocol admixture for a sufficient time and temperature to substantially remove the tocol from the third tocol admixture to produce a fourth tocol admixture comprising the removed tocol and a non-tocol component; and (d) extracting the tocol from the fourth tocol admixture with an extraction solvent comprising a polar, organic solvent that is miscible with water to produce a two phase system comprising a first phase containing a majority of the extraction solvent and a second phase, wherein the selectivity of the extraction solvent for the tocol with respect to the non-tocol component of the fourth tocol admixture is greater than unity, and removing the first phase from the second phase,
with the proviso that the extraction solvent is not a neat alcohol,
wherein step (b) can be conducted before step (c), or step (c) can be conducted before step (b), wherein steps (b) and (c) are conducted after step (a) and prior to step (d).

2. The method of claim 1, wherein the extraction solvent does not comprise an alcohol.

3. The method of claim 1, wherein step (b) is conducted before step (c).

4. The method of claim 1, wherein the esterifying compound comprises a sterol ester of fatty acid, sterol, triterpenoid alcohol, methyl-sterol, monoglyceride, diglyceride or triglyceride or a combination thereof.

5. The method of claim 1, wherein the heating step (a) is conducted at a temperature of from 70 to 300° C. and at a pressure of from 20 to 760 torr.

6. The method of claim 1, wherein the heating step (a) is conducted at a temperature of from 150 to 230° C. and at a pressure of from 20 to 200 torr.

7. The method of claim 1, further comprising removing water during the heating step.

8. The method of claim 1, further comprising adding a catalyst to the first tocol admixture prior to the heating step.

9. The method of claim 8, wherein the catalyst comprises an alkyl tin compound, a zinc salt of an organic acid, zinc oxide, a titanium (IV) alkoxide, or a mineral acid, or a combination thereof.

10. The method of claim 1, further comprising adding a second fatty acid to the first tocol admixture prior to heating step (a).

11. The method of claim 10, wherein the second fatty acid comprises a $C_{14}$ to $C_{22}$ fatty acid.

12. The method of claim 1, wherein prior to the heating step (a), an alcohol is not added to the first tocol admixture.

13. The method of claim 1, wherein the second tocol admixture is distilled in step (b) at a temperature of from 125 to 320° C. at a pressure of from 0.01 to 10 torr.

14. The method of claim 1, wherein the second tocol admixture is distilled in step (b) at a temperature of from 150 to 200° C. at a pressure of from 0.01 to 10 torr.

15. The method of claim 1, wherein after the distillation step (b) and prior to the distillation step (c), further distilling the third tocol admixture at a temperature of from 150 to 300° C. at a pressure of from 0.01 to 5 torr.

16. The method of claim 1, wherein the third tocol admixture is distilled in step (c) at a temperature of from 170 to 270° C. at a pressure of from 0.005 to 2 torr.

17. The method of claim 1, wherein steps (a)–(c) are conducted in series.

18. The method of claim 1, wherein steps (a)–(c) are conducted at from 1 to 24 hours.

19. The method of claim 1, wherein steps (a)–(c) are conducted at from 2 to 10 hours.

20. The method of claim 1, wherein the fourth tocol admixture has from 1 to 50% by weight tocols.

21. The method of claim 1, wherein the extraction solvent is an aqueous composition.

22. The method of claim 1, wherein the extraction solvent comprises acetic acid, propionic acid, acetone, aqueous methanol, aqueous ethanol, acetonitrile, aqueous 2-methoxyethanol, aqueous 2-ethoxyethanol, aqueous 2-propoxyethanol, 1,4-dioxane, dimethylacetamide, dimethylformamide, N-methyl pyrrolidinone, butadiene sulfone, dimethyl sulfoxide, 2-methoxyethyl ether, dimethoxyethane, or the aqueous solvent thereof, or a combination thereof.

23. The method of claim 1, wherein the extraction solvent comprises acetic acid, aqueous acetic acid, propionic acid, aqueous propionic acid, aqueous acetone, aqueous acetonitrile, aqueous 1,4-dioxane, aqueous dimethylacetamide, aqueous dimethylformamide, or a combination thereof.

24. The method of claim 1, wherein the extraction solvent comprises aqueous acetone.

25. The method of claim 1, wherein the extraction solvent comprises aqueous acetone, and the aqueous acetone comprises from 2 to 30% by weight water and from 70 to 98% by weight acetone, wherein the sum of the acetone and water is equal to 100%.

26. The method of claim 1, wherein the extraction solvent comprises aqueous acetone, and the aqueous acetone comprises from 7 to 25% by weight water and from 75 to 93% by weight acetone, wherein the sum of the acetone and water is equal to 100%.

27. The method of claim 1, wherein the extraction solvent comprises aqueous acetone, and the aqueous acetone comprises from 15 to 30% by weight water and from 70 to 85% by weight acetone, wherein the sum of the acetone and water is equal to 100%.

28. The method of claim 1, wherein the extraction solvent comprises aqueous acetone, and the aqueous acetone comprises from 20 to 26% by weight water and from 74 to 80% by weight acetone, wherein the sum of the acetone and water is equal to 100%.

29. The method of claim 1, wherein the extraction solvent comprises aqueous acetone, and the aqueous acetone comprises from 12 to 17% by weight water and from 83 to 88% by weight acetone, wherein the sum of the acetone and water is equal to 100%.

30. The method of claim 1, wherein the extraction solvent comprises aqueous acetonitrile.

31. The method of claim 1, wherein the extraction solvent comprises aqueous acetonitrile, and the aqueous acetonitrile comprises from 5 to 25% by weight water and from 75 to 95% by weight acetonitrile, wherein the sum of the acetonitrile and water is equal to 100%.

32. The method of claim 1, wherein the extraction solvent comprises aqueous acetic acid.

33. The method of claim 1, wherein the extraction solvent comprises aqueous acetic acid, and the aqueous acetic acid comprises from 5 to 15% by weight water and from 85 to 95% by weight acetic acid, wherein the sum of the acetic acid and water is equal to 100%.

34. The method of claim 1, wherein the extraction solvent comprises neat acetic acid.

35. The method of claim 1, wherein the extraction solvent comprises aqueous propionic acid.

36. The method of claim 1, wherein the extraction solvent comprises aqueous propionic acid, and the aqueous propionic acid comprises from 21 to 30% by weight water and from 70 to 79% by weight propionic acid, wherein the sum of the propionic acid and water is equal to 100%.

37. The method of claim 1, wherein the extraction solvent comprises aqueous methanol.

38. The method of claim 1, wherein the extraction solvent comprises aqueous methanol, and the aqueous methanol comprises from 7 to 15% by weight water and from 85 to 93% by weight methanol, wherein the sum of the methanol and water is equal to 100%.

39. The method of claim 1, wherein the extraction solvent comprises aqueous ethanol.

40. The method of claim 1, wherein the extraction solvent comprises aqueous ethanol, and the aqueous ethanol comprises from 17 to 30% by weight water and from 70 to 83% by weight ethanol, wherein the sum of the ethanol and water is equal to 100%.

41. The method of claim 1, wherein the extraction solvent comprises aqueous isopropanol.

42. The method of claim 1, wherein the extraction solvent comprises aqueous isopropanol, and the aqueous isopropanol comprises from 25 to 40% by weight water and from 60 to 75% by weight isopropanol, wherein the sum of the isopropanol and water is equal to 100%.

43. The method of claim 1, wherein the extraction solvent comprises aqueous 2-methoxyethanol.

44. The method of claim 1, wherein the extraction solvent comprises aqueous 2-methoxyethanol, and the aqueous 2-methoxyethanol comprises from 5 to 20% by weight water and from 80 to 95% by weight 2-methoxyethanol, wherein the sum of the 2-methoxyethanol and water is equal to 100%.

45. The method of claim 1, wherein the extraction solvent further comprises a halogenated or unhalogenated hydrocarbon solvent.

46. The method of claim 45, wherein the hydrocarbon solvent comprises a straight or branched $C_5$ to $C_{30}$ alkane, a straight or branched $C_5$ to $C_{30}$ alkene, an aromatic compound, or a combination thereof.

47. The method of claim 46, wherein the ratio of the extraction solvent to hydrocarbon solvent is from 1:20 to 20:1.

48. The method of claim 1, wherein the extraction step is conducted at from 0 to 100° C.

49. The method of claim 1, wherein the extraction step is conducted at from 45 to 55° C.

50. The method of claim 1, wherein the extraction step is a continuous, countercurrent extraction.

51. The method of claim 1, wherein the extraction step is batch.

52. The method of claim 1, wherein the extraction solvent to feed ratio is from 20:1 to 1:20.

53. The method of claim 1, further comprising after removing the first phase from the second phase, removing the extraction solvent from the first phase by evaporation or distillation.

54. The method of claim 1, wherein the first tocol admixture comprises vegetable oil deodorizer distillate.

55. The method of claim 44, wherein the vegetable oil deodorizer distillate comprises palm oil, rice bran oil, or soybean oil deodorizer distillate.

56. The method of claim 1, wherein the first tocol admixture comprises rice bran oil deodorizer distillate.

57. The method of claim 1, wherein (1) the first tocol admixture comprises rice bran oil deodorizer distillate; (2) the extraction solvent comprises aqueous acetone comprising 70 to 98% by weight acetone and from 2 to 30% by weight water, and (3) the extraction step is continuous and countercurrent.

58. The method of claim 1, further comprising after step (d) extracting tocotrienol from the first phase produced after step (d) with a third extraction solvent comprising a polar, organic solvent that is miscible with water to produce a two phase system comprising a third phase containing the majority of the third extraction solvent and a fourth phase, wherein the selectivity of the third extraction solvent for the tocotrienol with respect to the tocopherol is greater than one, and removing the third phase from the fourth phase, with the proviso that the third extraction solvent is not a neat alcohol.

59. The method of claim 58, wherein the tocotrienol is gamma-tocotrienol.

60. A method for separating a tocol from a tocol admixture comprising at least one tocol and a non-tocol component, comprising extracting the tocol from the tocol admixture with an extraction solvent comprising an aqueous composition comprising water and a polar, organic solvent that is miscible with water to produce a two phase system comprising a first phase containing a majority of the extraction solvent and a second phase, wherein the selectivity of the extraction solvent for the tocol with respect to the non-tocol component of the tocol admixture is greater than unity, and removing the first phase from the second phase, with the proviso that the extraction solvent does not comprise an alcohol.

* * * * *

UNITED STATES PATENT AND TRADEMARK OFFICE
CERTIFICATE OF CORRECTION

PATENT NO. : 6,159,347
DATED : December 12, 2000
INVENTOR(S) : SUMNER, JR. et al.

It is certified that error appears in the above-identified patent and that said Letters Patent is hereby corrected as shown below:

Claim 1, line 16, after the word "esterified" delete the term "ed".

Signed and Sealed this

First Day of May, 2001

Attest:

NICHOLAS P. GODICI

Attesting Officer        Acting Director of the United States Patent and Trademark Office